(12) United States Patent
Kim et al.

(10) Patent No.: US 10,725,043 B2
(45) Date of Patent: Jul. 28, 2020

(54) THREE-DIMENSIONAL FIBROBLAST AGGREGATE AND IN VITRO 3D SKIN DERMIS MODEL COMPRISING SAME

(71) Applicant: S-BIOMEDICS, Seoul (KR)

(72) Inventors: Sang Heon Kim, Seoul (KR); Jong Hoon Choi, Seoul (KR); Kwi Deok Park, Seoul (KR)

(73) Assignee: S-BIOMEDICS, Seoul (KR)

( * ) Notice: Subject to any disclaimer, the term of this patent is extended or adjusted under 35 U.S.C. 154(b) by 0 days.

(21) Appl. No.: 15/560,482

(22) PCT Filed: Apr. 19, 2016

(86) PCT No.: PCT/KR2016/004043
§ 371 (c)(1),
(2) Date: Sep. 21, 2017

(87) PCT Pub. No.: WO2017/082491
PCT Pub. Date: May 18, 2017

(65) Prior Publication Data
US 2018/0252715 A1    Sep. 6, 2018

(30) Foreign Application Priority Data

Nov. 12, 2015 (KR) .................. 10-2015-0159011

(51) Int. Cl.
| | | |
|---|---|---|
| *C07K 14/78* | (2006.01) | |
| *C12N 9/64* | (2006.01) | |
| *C12N 5/077* | (2010.01) | |
| *G01N 33/574* | (2006.01) | |

(52) U.S. Cl.
CPC .......... *G01N 33/574* (2013.01); *C07K 14/78* (2013.01); *C12N 5/0656* (2013.01); *C12N 9/64* (2013.01); *C12N 9/6421* (2013.01); *C12N 2501/115* (2013.01); *C12N 2513/00* (2013.01); *C12N 2533/52* (2013.01); *G01N 33/5743* (2013.01)

(58) Field of Classification Search
CPC .......... C12N 5/00; C12N 5/0656; C12N 9/64; C12N 9/6421
See application file for complete search history.

(56) References Cited

U.S. PATENT DOCUMENTS

2007/0269792 A1* 11/2007 Bernd .............. A61L 27/24
435/1.1

FOREIGN PATENT DOCUMENTS

| EP | 1290145 B1 | 11/2005 |
|---|---|---|
| JP | H03266980 A | 11/1991 |
| JP | H0489000 A | 3/1992 |
| JP | 2003146837 A | 5/2003 |
| JP | 2006333763 A | 12/2006 |
| JP | 2010172240 A | 8/2010 |
| JP | 2010193822 A | 9/2010 |
| JP | 201250406 A | 3/2012 |
| KR | 1020100122778 A | 11/2010 |

OTHER PUBLICATIONS

Furukawa et al., "Tissue engineered skin using aggregates of normal human skin fibroblasts and biodegradable material", J Artificial Organs, 2001, 4:353-356 (Year: 2001).*
Da Rocha-Azevedo, Bruno et al., "Fibroblast cluster formation on 3D collagen matrices requires cell contraction dependent fibronectin matrix organization", Experimental Cell Research, Oct. 29, 2012, pp. 546-555, vol. 319, No. 4, Elsevier Inc.
Gopu Sriram et al., "Fibroblast heterogeneity and its implications for engineering organotypic skin models in vitro", European Journal of Cell Biology, Aug. 2015, pp. 483-512, vol. 94, Elsevier GmbH.
Taihao Quan et al., "Elevated Matrix Metalloproteinases and Collagen Fragmentation in Photodamaged Human Skin: Impact of Altered Extracellular Matrix Microenvironment on Dermal Fibroblast Function", J Invest Dermatol, May 2013, pp. 1362-1366.
Korean Office Action for corresponding Korean Patent Application No. 10-2015-0159011 dated Feb. 20, 2017.
International Search Report dated Sep. 22, 2016 for PCT/KR2016/004043.
Hong Shen et al., "The immobilization of basic fibroblast growth factor on plasma-treated poly(lactide-co-glycolide)", Biomaterials, 2008, pp. 2388-2399, vol. 29, No. 15, Elsevier Ltd.
Lie Ma et al., "Incorporation of basic fibroblast growth factor by a layer-by-layer assembly technique to produce bioactive substrates", Journal of Biomedical Materials Research Part B: Applied Biomaterials, 2007, pp. 285-292.
Natalie L. Leong et al., "In vitro and in vivo evaluation of heparin mediated growth factor release from tissue-engineered constructs for anterior cruciate ligament reconstruction", Journal of Orthopaedic Research, Feb. 2015, pp. 229-236, vol. 33, No. 2.
The extended European search report for corresponding European Patent Application No. 16864417.7 dated Jun. 7, 2019.
Katsuko S. Furukawa et al., "Formation of Human Fibroblast Aggregates (Spheroids) by Rotational Culture," Cell Transplantation, 2001, pp. 441-445, vol. 10.
Korean Office Action for corresponding Korean Patent Application No. 10-2018-0114878 dated Jun. 25, 2019.
Chinese Office Action dated Jan. 2, 2020 of Chinese Patent Application No. 201680003627.X, which corresponds to the U.S. Appl. No. 15/560,482.
In Su Park, et al., "A novel three-dimensional adipose-derived stem cell cluster for vascular regeneration in ischemic tissue.," Cytotherapy, 2014, vol. 16, pp. 508-522.

(Continued)

*Primary Examiner* — Ruth A Davis
(74) *Attorney, Agent, or Firm* — Cantor Colburn LLP

(57) ABSTRACT

Provided are a three-dimensional (3D) fibroblast cluster, a method of preparing the same, an in vitro 3D skin dermis model including a fibroblast cluster cultured from a fibroblast, and a method of screening a drug by using the in vitro 3D skin dermis model.

14 Claims, 14 Drawing Sheets

(56) References Cited

OTHER PUBLICATIONS

Vincent Falanga, et al., "Low oxygen tension stimulates collagen synthesis and COL1A1 transcription through the action of TGF-beta1," Journal of cellular physiology, 2002, vol. 191, pp. 42-50.
Jung Mi Kang, et al. "Adhesion and differentiation of adipose-derived stem cells on a substrate with immobilized fibroblast growth factor," Acta Biomaterialia, 2012, vol. 3, pp. 1759-1767.
Office Action dated Jan. 28, 2020 of Japanese Patent Application No. 2018-503548, which corresponds to U.S. Appl. No. 15/560,482.

* cited by examiner

Scale bar: 500μm

THREE-DIMENSIONAL FIBROBLAST AGGREGATE AND IN VITRO 3D SKIN DERMIS MODEL COMPRISING SAME

TECHNICAL FIELD

The present invention relates to a three-dimensional (3D) fibroblast cluster, a method of preparing the same, an in vitro 3D skin dermis model including the 3D fibroblast cluster, and a method of screening a drug by using the in vitro 3D skin dermis model.

BACKGROUND

Cell therapeutics has been recently spotlighted as a new field of intractable disease treatment. Organ transplantation, gene therapy, or the like has been proposed before for the intractable disease treatment. However, due to immune rejection, short supply of organs, and lack of knowledge about vector development or pathological genes, such organ transplantation or gene therapy was not effectively put into practical use.

As an interest in cell therapeutics is on the rise, a transplant technique using in vitro proliferation of cells that are separated from a living body has been commercialized. In addition, artificial skin or reconstruction of cartilage or fibrous tissue has been put into practical use. Fibroblasts are cells that produce and maintain interstitial extracellular matrix (ECM), and fibroblasts are organically connected by ECM. In addition, fibroblasts are well known as cells that produce a variety of cytokines and physiologically active factors in terms of immune defense.

To utilize such fibroblasts as a cell therapeutic agent or a tissue engineering material, fibroblasts have been cultured two-dimensionally for mass proliferation, and then, treated with an enzyme, such as trypsin. However, in resulting fibroblasts, ECM produced therefrom was degraded so that the role of the ECM was not able to be expected at the transplantation stage. Meanwhile, studies have been carried out to culture various cells including fibroblasts into a three-dimensional (3D) cell cluster by using an artificial 3D porous ECM, called a scaffold that is fabricated by using a natural polymer or a biodegradable synthetic polymer, according to an engineering technique. However, due to limitations of materials in terms of a biodegradation rate or an inflammation reaction, it has difficulties in commercialization of a 3D cell cluster. Thus, a technique for inducing formation of a 3D cell cluster is required.

Skin tissue of the human body can be divided into three parts: epidermis which is the outermost skin layer; dermis which is a skin layer below epidermis; and hypodermis (or subcutaneous tissue). Among these parts, epidermis consists of epithelial cells and other melanin cells and immune cells, wherein the epithelial cells are differentiated into several layers from a basement membrane that is configured to firmly bind epidermis with dermis. Here, dermis under epidermis mainly consists of fibroblasts and several extracellular matrices secreted by the fibroblasts. Dermis is also known to be closely related to skin health and aging.

Collagen is a major protein that accounts for 90% of dermis, and is configured to maintain skin connective tissue and provide skin elasticity. In general, the number and function of fibroblasts decrease in accordance with external factors and aging, and such decreased number and function of fibroblasts are known to be the main cause of skin aging. The decrease in the number of cells reduces synthesis of fibrous components in skin tissue and causes loss of water and changes in stratum corneum. In addition, the increase in collagenase reduces cross-linked collagen, thereby reducing smoothness, moisture, and elasticity of the skin. The increased content and synthesis of collagen mean increased moisture and elasticity of the skin.

The degradation and synthesis of collagen in the skin matrix are controlled by a protease, for example, matrix metalloproteinase (MMP). Depending on a structure and functional characteristics, MMP is divided into various types. Type I collagen which is typical collagen in the skin is degraded by the action of MMP-1. The activity of MMP-1 is controlled by an inhibitor, such as TIMP-1 that is secreted to maintain skin homeostasis. Here, biomolecules, such as MMPs and TIMPs, are secreted by cells including fibroblasts. In addition, MMP-1 degrades extracellular matrix, thereby promoting tumor metastasis and progression. The synthesis and degradation of collagen by MMP-1 play an important role in cancer metastasis. Thus, a drug or substance targeting MMP-1/collagen is being developed to be utilized as a cancer therapeutic agent or a cosmetic composition.

In addition, MMP is known to be overexpressed in pathological conditions, such as an inflammatory disease including arthritis, or cancer including cancer metastasis, so that an MMP inhibitor targeting MMP has been developed as a therapeutic agent for the diseases above.

In this regard, 2D cell-based assays for screening a drug targeting MMP or collagen have been developed. However, such 2D cell-based assays are limited due to drug sensitivity, drug penetration into cells and tissues, or the like, and are inadequate to accurately predict the response in living organisms. In addition, due to the structural and functional complexity of the skin, skin research using a single type of skin cells has limitations. A skin model having a 3D structure designed to overcome limitations uses artificial skin, but existing artificial skin is difficult to screen a drug at a high speed. Therefore, development of a new skin model system that can screen a drug at a high speed for high-throughput and mimic the skin environment is required.

DETAILED DESCRIPTION OF THE INVENTION

Technical Problem

An aspect of the present invention provides a method of producing a fibroblast cluster, the method including: culturing fibroblasts in a culture broth container having a surface coated with a protein having fibroblast-binding activity to thereby obtain a culture including a fibroblast cluster that is formed by delocalizing the cultured fibroblasts from the surface; and separating the fibroblast cluster from the culture, wherein binding between the protein having fibroblast-binding activity and fibroblasts is weaker than binding between fibroblasts.

Another aspect of the present invention provides a fibroblast cluster produced according to the method above.

Another aspect of the present invention provides an in vivo three-dimensional (3D) skin dermis model including a fibroblast cluster cultured from fibroblasts.

Another aspect of the present invention provides a method of preparing an in vitro three-dimensional (3D) artificial skin model, the method including: culturing fibroblasts in a culture broth container having a surface coated with a protein having fibroblast-binding activity to thereby obtain a culture including a fibroblast cluster that is formed by delocalizing the cultured fibroblasts from the surface, wherein binding between the protein having fibroblast-binding activity and fibroblasts is weaker than binding between fibroblasts; and further culturing the fibroblast cluster of the culture for at least 12 hours.

Another aspect of the present invention provides a method of screening a substance that decreases expression or activity of matrix metalloproteinase (MMP), the method including: treating a test substance with the fibroblast cluster or the dermis model; measuring a level of expression or activity of MMP in the fibroblast cluster or the skin dermis model, each treated with the test substance; comparing the measured level of expression or activity of MMP with that of an untreated control group; and selecting a substance that decreases expression or activity of MMP as compared with the control group.

Another aspect of the present invention provides a method of screening a substance that decreases expression or activity of collagen, the method including: treating a test substance with the fibroblast cluster or the in vitro 3D skin dermis model; measuring a level of expression or activity of collagen in the fibroblast cluster or the skin dermis model; comparing the measured level of expression or activity of collagen with that of an untreated control group; and selecting a substance that increases expression or activity of collagen as compared with the control group.

Technical Solution

An aspect of the present invention provides a method of producing a fibroblast cluster, the method including: culturing fibroblasts in a culture broth container having a surface coated with a protein having fibroblast-binding activity to thereby obtain a culture including a fibroblast cluster that is formed by delocalizing the cultured fibroblasts from the surface; and separating the fibroblast cluster from the culture, wherein binding between the protein having fibroblast-binding activity and fibroblasts is weaker than binding between fibroblasts.

Another aspect of the present invention provides a culture container for forming a fibroblast cluster, the culture container having a surface coated with a protein having fibroblast-binding activity, wherein fibroblasts in a culture broth are adhered to the surface, and binding between the protein having fibroblast-binding activity and fibroblasts is weaker than binding between fibroblasts.

The term "fibroblast" (used interchangeably with the term 'fiber cell') used herein refers to a cell constituting a component of fibrous connective tissue, and may be a cell of connective tissue of a mammal. Fibroblasts can produce extracellular matrix and collagen, and can serve to heal wounds, for example, skin scars, burns, pressure sores, or cut wounds.

The term "fibroblast cluster" or "three-dimensional (3D) fibroblast cluster" (used interchangeably with the term 'fibroblast cellular tissue') used herein refers to a state in which two or more cells are aggregated, and may be in the form of a tissue or in the form of single cells. Each cell cluster may be present in the tissue itself or in a part thereof, or may be present as a cluster of single cells. The cell cluster may include fibroblast-like cellular tissue. In addition, the term "three-dimensional (3D)" refers to a structure having a model with three geometric parameters (for example, depth, width, and height, or X-, Y-, and Z-axes) rather than two dimensional parameters. In this regard, the fibroblast cluster according to an embodiment may be cultured in a 3D manner. That is, the fibroblast cluster may refer to a fibroblast cluster consisting of cells that are adhered to a culture container, cultured in a floating state, and three-dimensionally formed into spheres, sheets, or similar three-dimensional forms (for example, a similar cellular tissue). In addition, the fibroblast cluster according to an embodiment may refer to a 3D fibroblast cluster formed by itself without the need to use an artificial 3D porous extracellular matrix, for example, a biodegradable synthetic polymer support such as a sheet, a hydrogel, a thin film, and a scaffold, or a natural polymeric support, prepared by using tissue engineering techniques wherein the tissue engineering technique is distinguished from the 3D fibroblast cluster according to an embodiment in which the matrix, rather than the cell, is 3D.

The seeding of the fibroblasts into the culture container may include all acts performed to culture the fibroblast in the culture container, the acts including addition of the fibroblasts to the culture container or adhesion of the fibroblasts into the culture container.

The term "adhesion or binding of cells" used herein refers to adhesion or binding between cells, between cells and the culture container, or between surfaces of biomaterials. The adhesion or binding between cells on the culture container or on the surface of the biomaterial may have various mechanisms. For example, there are specific cell adhesion mediated by biological recognition, and nonspecific cell adhesion dependent on electrostatic or surface energy. The specific cell adhesion may refer to adhesion occurring by binding specific peptides (for example, arginine-glycine-aspartid acid; RGD) present in the extracellular matrix (ECM) proteins, such as collage, fibronectin, and laminin, to receptors present in the cell membrane. The nonspecific cell adhesion may refer to adhesion of cells by inducing a cell surface to be electrically positively adhered to a cell membrane having electrically negative phospholipids.

The culture container may include a hydrophobic surface, for example, a surface having a water contact angle in a range of about 90° to about 150°, and may include a surface coated with a protein having adhesive or binding activity to the fibroblasts. The culture container having a modified surface may have a surface on which a bond between a cell and an substrate (for example, a protein or growing factor having binding activity to cells coated on the surface of the culture container) is more weakly induced than a bond between cells. Unlike blood cells, the fibroblasts are adhesion-dependent cells, such as epithelial cells or mesenchymal cells that adhere to the extracellular matrix and grow thereon. If the cells do not adhere to an adherent matrix, cell death is induced, and such cell death is referred to as anokis. In the culturing method according to an embodiment, cell death is not induced in the adhesion or binding between a cell and an adherent matrix, but the adhesion or binding between a cell and an adherent matrix is more weakly induced that the adhesion or binding between cells. In this regard, the cells are not cultured into a two-dimensional (2D) monolayer. That is, the fibroblast induce weak adhesion or binding between a cell and an adherent matrix is induced in the fibroblasts at the beginning of the culture, and cell-to-cell adhesion or binding is also induced, resulting in the formation of a 2D fibroblast cluster by binding between these cells. As the culturing time increases, the 2D fibroblast cluster is detached or delocalized from the surface of the culture container, and the detached or delocalized 2D fibroblast cluster is continuously cultured in a floating state, thereby forming a 3D fibroblast cluster.

A method of modifying the surface of the culture container so as to induce the cell-to-adherent matrix (for example, a protein or growing factor having binding activity to cells coated on the surface of the culture container) adhesion or binding is induced more weakly than the cell-to-cell adhesion or binding may be induced by using a protein having binding activity to the fibroblast.

The cell-to-adherent matrix adhesion or bonding may be strongly induced by a protein, for example, collagen, fibronectin, and laminin, binding to an integrin present in the cell membrane of the fibroblast. The term "integrin" used herein refers to a receptor molecule that acts when cells that are present in the cell membrane and adhere to the extracellular matrix including fibronectin and collagen, For example, the integrin may be a transmembrane glycoprotein, which is a heterodimer consisting of two α or β subunits, and may include all types of integrins. Therefore, binding between the protein having binding activity to the fibroblast and the fibroblasts may be weaker than binding between the fibroblast and the fibronectin. In addition, the protein having activity to the fibroblast bind to the fibroblast at activity levels in a range of about 60% to about 95%, for example, 60%, 70%, 80%, 90%, or 95%, as compared to the binding between the fibroblast and the fibronectin, in the medium. Therefore, the protein having binding activity to the fibroblast may include proteins that do not bind to integerins. In addition, in one embodiment, proteins not binding to integerin may include proteins binding to heparan sulfate proteoglycan present in the cell membrane of the fibroblast. In one embodiment, the protein binding to the heparan sulfate proteoglycan may be a fibroblast growth factor (FGF), and in addition, may be immobilized on the surface of the culture container at a concentration in a range of about 5 µg/ml to about 100 µg/ml.

The term "fibroblast growth factor (FGF)" used herein refers to a type of growth factors, and may be a growth factor that stimulates fibroblasts to induce proliferation thereof. The FGF is a heparin-binding protein, and as described above, may interact with heparan sulfate proteoglycan of the fibroblast. FGF have 22 types thereof, and for example, may include FGF 1, 2, 3, 4, 5, 6, 7, 8, 9, 10, 11, 12, 13, 14, 15, 16, 17, 18, 19, 20, 21, or 22. Although the type of FGF is different in name, FGF may include all types thereof, as long as the types can be recognized as the same protein by one of ordinary skill in the art. For example, FGFs 11, 12, 13, and 14 are each also known as "iFGF", and FGF 15 is also known as "FGF 15/19". In addition, for example, FGF 1 or 2 may include "heparin-binding growth factor 1 (HBGF-1)" or "heparin-binding growth factor 2 (HBGF-2)".

The immobilization of the protein binding to the fibroblast onto the surface of the culture container may be utilized to immobilize a polypeptide onto a solid matrix surface and may be accomplished by any method known in the art. For example, the immobilization method may include physical adsorption or covalent bonding by non-selective chemical reaction. Examples of the immobilization method include: a method of immobilizing proteins using biotin-streptavidin/avidin bonds by binding biotin to a protein and then applying the protein to a solid surface treated with streptavidin or avidin; a method of immobilizing proteins by integrating active groups (chemical functional groups for immobilizing proteins by chemical bonding) on a substrate using plasma; a method of immobilizing proteins by physical adsorption to a porous thin film after forming a porous sol-gel thin film having a specific surface area sufficiently increased by using a sol-gel method on a solid substrate; a method of immobilizing antithrombogenic proteins on a surface of polytetrafluoroethylene (PTFE) by plasma reaction; a method of immobilizing proteins by binding an enzyme in which two or more cationic amino residues are fused to two enzymes continuously; a method of immobilizing proteins on a hydrophobic polymer layer bonded to a solid support using a substrate; a method of immobilizing proteins on a plastic surface using buffer components; and a method of immobilizing proteins by contacting proteins to a solid surface including a hydrophobic surface in an alcohol solution.

In addition, a polypeptide linker that can be subjected to recombinant mass expression and easy purification may be used to perform immobilization in the form of a peptide linker-growth factor (for example, FGF) recombinant protein in which an amino terminus of the growth factor (for example, FGF) is fused to a carboxyl terminus of the polypeptide linker. For example, by using the polypeptide linker, the growth factor may be immobilized on a hydrophobic surface in the form of a recombinant protein while maintaining the biological activity inherent to the growth factor. Then, by using adhesion activity of the fibroblasts to the hydrophobic surface, the fibroblasts may be adhered to the hydrophobic surface, thereby leading to efficient culture of the fibroblasts on the hydrophobic surface.

A substance capable of binding to an amino terminus of a growth factor through a carboxyl terminus of the polypeptide linker and adsorbing to a culture container including a hydrophobic surface through a hydrophobic domain present at an amino terminus of the polypeptide linker, or a substance that can be subjected to recombinant mass expression and easy purification without being adversely affected, may be suitable for use as the polypeptide linker in the present invention. Examples of the polypeptide linker are maltose-binding protein (MBP), a hydrophobin, a hydrophobic cell penetrating peptide (CPP), and the like.

MBP (NCBI GenBank Accession No. AAB59056) may refer to a periplasm protein that is located in the periplasm across the cell membrane of *Escherichia coli* and involved in the migration of saccharides, such as maltose or maltodextrin, into cells. MBP is mainly used for the production of useful exogeneous proteins into recombinant proteins, and is decoded and produced from male gene in the cell. When genes of an exogeneous protein are inserted into downstream of the cloned malE gene and expressed in the cell, a recombinant protein in which two proteins are combined can be easily produced in high yields. In particular, when proteins to be expressed are exogeneous proteins that are small or less stable in other host cells, it is advantageous to express such exogeneous proteins in a recombinant protein form using MBP. As such, the exogeneous proteins expressed from the malE-fused genes can be isolated based on the characteristics that MBP has binding affinity to maltose. For example, a resin coated with amylase, which is a poly-maltose, may be reacted with a cell homogenate. Then, the reacted resin may be washed several times to remove other contaminated proteins, and a high concentration of maltose may be added to the resin to compete, thereby eluting only the desired protein.

The MBP-cell adhesive substrate (for example, a growth factor) recombinant protein may be prepared by using chemical synthesis or genetic recombination technology typically used in the art, or may obtained by recovering the recombinant protein after culturing transformed bacteria expressing the recombinant protein under suitable conditions. The MBP-cell adhesive substrate recombinant protein thus obtained may be immobilized onto a culture container including a hydrophobic surface without requiring any special treatment. That is, the recombinant protein may be spontaneously immobilized via physical adsorption of the hydrophobic domain positioned in the amino terminus of the polypeptide linker of the same recombinant protein to the hydrophobic surface.

In addition, a method of inducing cell-to-adhesive substrate (for example, a protein having fibroblast-binding activity) adhesion or binding relatively weakly as compared with cell-to-cell adhesion or binding may be induced by treating a substance that can weaken adhesion or binding between fibroblasts and a substrate (for example, a surface of a culture container).

The culture container including a hydrophobic surface, for example, a culture container having a culture with a water contact angle in a range of about 90° to about 150°, may be a cell culture container that is surface-treated with a polymer that imparts hydrophobicity to a conventional cell culture container, or a cell culture container formed of such a polymer. Such a hydrophobic polymer may be, although not limited thereto, at least one selected from polystyrene, polymethyl methacrylate (PMMA), polyethylene terephthalate (PET), polyvinyl chloride (PVC), polyethylene (PE), polypropylene (PP), poly(tetrafluoroethylene) (PTFE), and an aliphatic polyester-based polymer selected from poly(L-lactic acid) (PLLA), poly(D,L-lactic acid) (PDLLA), poly(glycolic acid) (PGA), poly(caprolactone) (PCL), poly(hydroxyalkanoate), polydioxanone (PDS), and poly(trimethylene carbonate), or may be a copolymer of the units above, such as poly(lactic acid-co-glycollic acid) (PLGA), poly(L-lactic acid-co-caprolactone) (PLCL), poly(glycolic acid-co-caprolactone) (PGCL), or a derivative thereof. In addition, the culture container according to an embodiment may have a hydrophobic silanized surface, a carbon nanotube (CNT) surface, a hydrocarbon-coated surface, or a metallic (for example, stainless steel, titanium, gold, and platinum, etc) surface.

Before seeding the fibroblasts into the culture container, the fibroblasts may be cells proliferated through passage culture. As a method of cell proliferation through passage culture, the fibroblasts isolated by a known method may be subjected to proliferation through passage culture according to a known method. For example, as the isolated fibroblasts, cells cultured through 1 passage or cells cultured through 10 or more passages may be used for subsequent formation of a 3D fibroblast cluster.

The fibroblasts may be seeded at a concentration in a range of about $1.0 \times 10^4$ cells/cm$^2$ to about $2.0 \times 10^5$ cells/cm$^2$. In addition, for example, the cell concentration may be in a range of about $7.5 \times 10^4$ cells/cm$^2$ to about $1.5 \times 10^5$ cells/cm$^2$, or may be about $1.25 \times 10^5$ cells/cm$^2$. When the cell concentration is $1.0 \times 10^4$ cells/cm$^2$ or more, a 3D cell cluster may be formed. When the cell concentration is $1.25 \times 10^5$ cells/cm$^2$ or more, a 3D cell cluster having a size that can be distinguishable with the naked eye may be formed.

In addition, the culture period may be 1 day to 1 week. As a medium suitable for the culture, a serum-containing or serum-free medium conventionally used for culture and/or differentiation of fibroblasts may be used without limitation, and examples thereof are a Dulbeco's modified eagle medium (DMEM), Ham's F12, or a medium in which serum is added to a mixture of the above substances.

As described above, the forming of fibroblasts into the 3D fibroblast cluster may be performed as follows: a 2D fibroblast cluster initially formed by cell-to-adhesive substrate binding is delocalized from the surface of the culture container, and then, the delocalized 2D fibroblast cluster is continuously cultured in a floating state in the culture container.

The fibroblast cluster formed through adhesion of the fibroblast to the surface of the culture container has a diameter detectable with the naked eye. In this regard, the formed fibroblast cluster may be separated by using a pipette, or recovered by a method such as filtration or centrifugation. That is, the recovering of the formed fibroblast cluster from the culture container may be performed without treatment of an enzyme. The 3D cell cluster thus obtained may be subjected to enzymatic treatment with collagenase, trypsin, or dispase, mechanical treatment with pressure, or combinational treatment, to thereby break up the cluster form into the form of single cells, or the 3D cell cluster form itself may be used.

Another aspect of the present invention provides a fibroblast cluster prepared according to the method above.

The method of preparing the fibroblast cluster is the same as described above.

The fibroblast cluster may be in the form of spheres or sheets, each having a size detectable with the naked eye. For example, the fibroblast cluster may be in the form of spheres having a diameter in a range of about 300 μm to about 2,000 μm. In one embodiment, the fibroblast cluster may be in the form of spheres having a diameter in a range of about 300 μm to about 1,000 μm. The diameter of the fibroblast cluster in the form of spheres may be adjusted by one of ordinary skill in the art to a size that can be distinguishable with the naked eye by using the culture method according to an embodiment. In addition, the fibroblast cluster in the form of spheres according to an embodiment may include fiber cells having a diameter within about 400 μm at a concentration in a range of about $3.0 \times 10^5$ cells to about $1.0 \times 10^6$ cells. In addition, in one embodiment, the fibroblast cluster may secret endothelial growth factor (EGF), extracellular matrix (ECM), or vascular endothelial growth factor (VEGF).

Therefore, the fibroblast cluster according to an embodiment may be utilized as a useful cell source in supplying a cell therapeutic agent or a physiologically active substance. The use of the fibroblast cluster is as follows.

Another aspect of the present invention provides cell therapeutic agent for skin regeneration or angiogenesis, the agent including the fibroblast cluster according to an embodiment.

In addition, there is provided a pharmaceutical composition for preventing or treating skin scars, burns, bedsores, or ischemic diseases, the composition including the fibroblast cluster or a culture broth thereof as an effective ingredient.

As described above, the fibroblast cluster may secret EGF, ECM, or VEGF. In this regard, the fibroblast cluster may be transplanted into an individual in need thereof, and serve as a cell source, to thereby stimulating skin regeneration or angiogenesis. Accordingly, the fibroblast cluster may be useful in the pharmaceutical composition for preventing and treating skin scars, burns, bedsores, or ischemic diseases. The ischemic diseases include, for example, ischemic heart disease, ischemic myocardial infarction, ischemic heart failure, ischemic enteritis, ischemic vascular disease, ischemic eye disease, ischemic retinopathy, ischemic glaucoma, ischemic renal failure, ischemic androgenetic alopecia, ischemic stroke, and ischemic peripheral disease.

A dosage of the cell therapeutic agent or the pharmaceutical composition according to an embodiment may be in a range of about $1.0 \times 10^5$ cells/kg to about $1.0 \times 10^8$ cells/kg (weight), or about $1.0 \times 10^7$ cells/kg to about $1.0 \times 10^8$ cells/kg (weight) with respect to the fibroblast cluster constituting a cell cluster that is an active ingredient. However, such a dosage varies depending on factors, such as a formulation method, an administration way, a patient's age, weight, gender, or pathological condition, food, administration time, an administration route, an excretion rate, and reaction responsiveness, but one of ordinary skill in the art will appropriately adjust a dosage in consideration of such factors above. The number of administrations may be 1 or 2 or more within the range of clinically acceptable side effects, and the administration site may be one or two or more. For an animal other than a human, the dosage may be the same as that of human per kg, or for example, the dosage may be calculated in terms of a volume ratio (e.g., an average value) of organs (e.g., a heart) of a target animal and a human to be administered. A target animal to be treated according to an embodiment may be a human or a mammal for other purposes, and examples thereof are a human, monkey, rat, rabbit, sheep, cow, dog, horse, and pig.

The cell therapeutic agent or pharmaceutical composition according to an embodiment may include, as an active ingredient, a cell cluster and a pharmaceutically acceptable carrier and/or additive. Examples of the active ingredient are sterilized water, physiological saline solution, a common buffering agent (e.g., phosphoric acid, citric acid, or other organic acids), a stabilizer, a salt, an antioxidant (e.g., ascorbic acid), a surfactant, a suspending agent, an isotonic agent, a preservative, and the like. For local administration, it is also preferable to combine an organic substance, such as a biopolymer, an inorganic substance, such as hydroxyapatite, specifically, a collagen matrix, a polylactic acid polymer or copolymer, a polyethylene glycol polymer or copolymer, and a chemical derivative thereof. When the cell therapeutic agent or pharmaceutical composition according to an embodiment is prepared in a formulation suitable for injection, a cell cluster may be dissolved in a pharmaceutically acceptable carrier or frozen in a solution state in which a cell cluster is dissolved.

The cell therapeutic agent or pharmaceutical composition according to an embodiment may appropriately include, if necessary, a suspending agent, a solubilizer, a stabilizer, an isotonic agent, a preservative, an anti-adsorption agent, a surfactant, a diluents, an excipient, a pH adjuster, a painless agent, a buffering agent, a reducing agent, and an antioxidant, depending on the administration method or formulation. In addition to the examples above, pharmaceutically acceptable carriers and formulations suitable for the present inventive concept are described in detail in the following document [Remington's Pharmaceutical Sciences, 19th ed., 1995].

The cell therapeutic agent or pharmaceutical composition according to an embodiment may be prepared by using a pharmaceutically acceptable carrier and/or excipient according to a method that can be easily carried out by one of ordinary skill in the art, so as to be formulated in a unit dosage form or prepared in a multi-dose container. Here, the formulations may be in the form of oil or solutions, suspensions, or emulsions in aqueous media, or in the form of powder, granule, tablet, or capsule.

Another aspect of the present invention provides a tissue engineering support in which the fibroblast cluster according to an embodiment is loaded on a biodegradable polymer scaffold.

As described above, since the fibroblast cluster according to an embodiment can secret endothelial growth factor, extracellular matrix, or vascular endothelial growth factor, the fibroblast cluster in a state being loaded on a scaffold may be transplanted into an individual in need of the fibroblast cluster, to thereby promote skin regeneration or angiogenesis. The tissue engineering support may be configured in a way that the fibroblast cluster is loaded on a support made by molding a biodegradable polymer.

The biodegradable polymer is spontaneously and slowly degraded in a living body in a certain period of time, and may include at least one property selected from biocompatibility, blood affinity, anti-petrifaction property, cell nutrition, and intercellular matrix formation ability. Although not particularly limited herein, representative types of the biodegradable polymer include fibrin, gelatin, chitosan, alginate, hyaluronic acid, dextran, poly(lactic acid), poly(glycolic acid) (PGA), poly(lactic-co-glycolic acid) (PLGA), poly-ε-(caprolactone), polyanhydride, polyorthoester, polyvinyl alcohol, polyethylene glycol, polyurethane, poly(acrylic acid), poly(N-isopropylacrylamide), poly(ethylene oxide)-poly(propylene oxide)-poly(ethylene oxide) copolymer, a copolymer thereof, a mixture thereof, and the like. Here, an amount of the biodegradable polymer in a composite support may be in a range of about 5 weight % to about 99 weight % in view of the molding of the support or the loading of the cell cluster. The composite support may be manufactured by molding the biodegradable polymer according to a know method, such as a solvent-casting and particle-leaching technique, a gas forming technique, a fiber extrusion and fabric forming process, a thermally induced phase separation technique, an emulsion freeze drying method, a high pressure gas expansion, or the like.

The support molded and manufactured as described above may serve to transfer the loaded cell cluster into the grafted tissue and allow the cells to adhere and grow in a 3D manner, to thereby form a new tissue. Here, the size and structure of pores in the support may be influenced by adhesion growth of the cells on the composite support, and in this regard, in order for a nutrient solution to penetrate evenly into the support to allow the cells to grow well, the pores in the support may have an inter-connecting structure. In addition, the pores in the support may have an average particle diameter in a range of about 50 μm to about 600 μm.

Another aspect of the present invention provides a 3D drug-screening culture system for screening a drug, the system including the fibroblast cluster according to an embodiment.

The 3D fibroblast cluster has an artificial cell form that mimics the environment in the living body, and can be effectively used for actual cell morphology and function studies, or therapeutic agents (for example, the above-described skin diseases or vascular diseases). Therefore, the 3D drug-screening culture system including the fibroblast cluster may replace animal experiments performed for the efficacy test of medicines or cosmetics as therapeutic agents for disease, or for inflammation and allergy test.

Another aspect of the present invention provides an in vitro 3D skin dermis model including the fibroblast cluster cultured from the fibroblasts.

Another aspect of the present invention provides an in vitro model for screening expression of a drug, for example, an MMP inhibitor or an enhancer for expression or activity of collagen within a cell, the model including the fibroblast cluster cultured from the fibroblasts.

Another aspect of the present invention provides a method of preparing an in vitro 3D artificial model or an in vitro model for screening an MMP inhibitor or an enhancer for expression or activity of collagen within a cell, the method including: culturing fibroblasts in a culture broth container having a surface coated with a protein having fibroblast-binding activity to thereby obtain a culture including fibroblast clusters formed by delocalizing the cultured fibroblasts from the surface, wherein binding between the protein having fibroblast-binding activity and fibroblasts is weaker than binding between fibroblasts; and further culturing the fibroblast cluster from the obtained culture for at least 12 hours.

The fibroblast cluster and the method of preparing the same are the same as described above.

In one embodiment, the present inventive concept provides a drug-screening composition or model including the fibroblast cluster cultured from the fibroblasts. The drug may be a skin anti-aging agent or a therapeutic agent for an inflammatory disease, arthritis, or cancer. Thus, for example, the in vitro 3D skin dermis model including the fibroblast cluster cultured from the fibroblasts may be used for screening a therapeutic agent for an inflammatory disease, arthritis, or cancer.

In one embodiment, the fibroblast cluster may exhibit pathological characteristics depending on skin aging. For example, the fibroblast cluster may be associated with decreased expression or activity of collagen, or increased expression or activity of MMP. The fibroblast cluster may be further associated with decreased expression or activity of fibronectin, or increased expression or activity of elastin. In the present specification, the increased or decreased expression or activity refers to increased or decreased expression or activity of the proteins or genes described above as compared with normal cells or fibroblast cultured two-dimensionally. The collagen may have types I, II, III, IV, V, VI, VII, VIII, IX, X, XI, XII, XIII, or XIV. In addition, MMP may include at least one of MMPs 1 to 28.

As described in the background of the present specification, the decreased collagen can cause low synthesis of fibrous components in skin tissue, loss of water in skin tissue, and changes in stratum corneum. In addition, the collagen may be degraded by MMP. Thus, the fibroblast cluster associated with decreased activity or activity of collagen or increased expression or activity of MMP may be utilized when screening a skin anti-aging drug. For example, such a skin anti-aging drug may be a drug having skin moisturizing effect, increased elasticity, decreased wrinkles, and antioxidant activity. In addition, MMP may degrade an extracellular matrix, thereby promoting tumor metastasis and progression. The MMP-dependent collagen synthesis and degradation may play a role in cancer metastasis. In addition, MM is known to be overexpressed in pathological conditions, such as inflammatory diseases including arthritis or cancer including cancer metastasis, and thus, MMP inhibitors targeting MMP have been developed as therapeutic agents for the above-mentioned diseases. Therefore, the fibroblast cluster associated with decreased expression or activity of collagen or increased expression or activity of MMP according to an embodiment may be utilized when screening therapeutic agents for inflammatory diseases, arthritis, or cancer. The inflammatory diseases may be selected from the group consisting of dermatitis, conjunctivitis, peritonitis, periodontitis, rhinitis, tympanitis, laryngopharyngitis, tonsilitis, pneumonia, gastric ulcer, gastritis, Crohn's disease, colitis, hemorrhoids, gout, ankylosing spondylitis, rheumatic fever, lupus, fibromyalgia, psoriatic arthritis, osteoarthritis, rheumatoid arthritis, frozen shoulder, tendinitis, tenosynovitis, peritendinitis, myositis, hepatitis, cystitis, nephritis, sjogren's syndrome, multiple sclerosis, and acute and chronic inflammation diseases. In addition, arthritis may be osteoarthritis or rheumatoid arthritis. The cancer therapeutic agent includes not only a substance that inhibits the proliferation of cancer cells, but also a substance that inhibits cancer metastasis.

The differentiation of the fibroblasts may be performed by culturing the fibroblast cluster from the fibroblasts through adhesion of the fibroblasts to a culture container including a hydrophobic surface. In detail, when the fibroblasts are cultured through adhesion to a culture contain including a hydrophobic surface, the adhered fibroblasts may be separated from the culture container as a density of the fibroblasts increases, to thereby form a fibroblast cluster. In addition, following the culturing of the fibroblasts or the forming of the fibroblast cluster, the fibroblast cluster may be further cultured for at least 12 hours or at least 1 day, for example, for 12 hours to 15 days, for 1 day to 15 days, for 3 days for 10 days, for 3 days to 7 days, or for 5 days to 7 days. As a suitable medium suitable for the culturing of the fibroblasts, a serum-containing or serum-free medium conventionally used for culturing and/or differentiation of the fibroblasts may be used without limitation, and examples thereof are a Dulbeco's modified eagle medium (DMEM), Ham's F12, or a medium in which serum is added to a mixture of the above-mentioned substances. A detailed description of a method of forming a cell cluster through culturing will be described below.

Since the fibroblast cluster cultured from the fibroblasts according to an embodiment can mimic in vivo environments as being cultured three-dimensionally and includes the extracellular matrix, the fibroblast cluster can be utilized as an in vitro skin dermis model. The term "skin dermis model" (used interchangeable with the term 'dermal equivalent') used herein refers to a modeled structure or shape of dermal tissue or dermis, and may also refer to a model designed in consideration of determining interactions between cells in the dermis, or relationship between the structure and the morphology of cells in the dermis.

Another aspect of the present invention provides a method of screening a substance that decreases expression or activity of MMP, the method including: treating a test substance with the fibroblast cluster or the in vitro 3D skin dermis model; measuring a level of expression or activity of MMP in the fibroblast cluster or the in vitro 3D skin dermis model treated with the test substance; comparing the measured level of expression or activity of MMP with that of an untreated control group; and selecting a substance that decreases expression or activity of MMP as compared with the control group.

Another aspect of the present invention provides a method of screening a substance that increases expression or activity of collagen, the method including: treating a test substance with the fibroblast cluster or the in vitro 3D skin dermis model; measuring a level of expression or activity of collagen in the fibroblast cluster or the in vitro 3D skin dermis model treated with the test substance; comparing the measured level of expression or activity of collagen with that of an untreated control group; and selecting a substance that decreases expression or activity of collagen as compared with the control group.

In the method of screening above, the test substance may include one selected from the group consisting of a low-molecular weight compound, an antibody, an antisense nucleotide, a short interfering RNA, a short hairpin RNA, a nucleic acid, a protein, a peptide, and other extracts and natural substances.

The treating of the test substance may include contacting the test substance with the fibroblast cluster or the in vitro 3D skin dermis model. The contacting of the test substance may include, for example, injecting a solution containing the test substance at a certain concentration to each well containing one or more fibroblast clusters of the in vitro 3D skin dermis model.

The measuring of the level of expression or activity of MMP or collagen may be performed by one method selected from the group consisting of reverse transcriptase polymerase chain reaction (RT-PCR), enzyme linked immunosorbent assay (ELISA), immunohistochemistry, western blotting, immunoprecipitation, immunofluorescence, and fluorescence-activated cell sorting (FACS). In addition, the measuring of the level of expression or activity of MMP or collagen may be performed by measuring an amount of MMP or collagen secreted in a culture broth, and the amount of collagen in the culture broth may be measured by hydroxyproline assay.

By comparing the measured level of expression or activity of MMP with that of an untreated control group, a substance that decreases expression or activity of MMP as compared with the control group may be selected as an inhibitor of MMP expression or activity, or a candidate substance. Such a substance that decreases expression or activity of MMP or a candidate substance may be a skin anti-aging substance or a cancer therapeutic agent. In addition, by comparing the measured level of expression or activity of collagen with that of an untreated control group, a substance that increases expression or activity of collagen as compared with the control group may be selected as an inhibitor of collagen expression or activity, or a candidate substance. Such a substance that decreases expression or activity of collagen or a candidate substance may be a skin anti-aging substance or a cancer therapeutic agen.

In one embodiment, the fibroblast cluster cultured from the fibroblasts may show decreased expression or activity of collagen or increased expression or activity of MMP. Thus, the fibroblast cluster according to an embodiment may be utilized for screening a substance related to expression or activity of collagen or MMP.

In one or more embodiments, the present inventive concept provides a drug-screening device equipped with a well plate including at least one well, wherein one or more fibroblast clusters are seeded per well. The fibroblast cluster is the same as described above.

In addition, the present inventive concept provides a method of screening a drug, the method including: injecting a solution containing a candidate substance per well of a cell plate included in the drug-screening device; culturing the well plate to which the candidate substance is injected; collecting a fibroblast cluster from the well plate or recovering a culture broth from the well plate; and performing assay on the collected fibroblast cluster or on the culture broth. Here, the candidate substance may be identical to or different from the candidate substance described above. Regarding the culturing of the well plate, culture time and temperature may be arbitrarily determined by one of ordinary skill in the art. The assay performed herein may be, for example, MMP secretion assay using ELISA on the culture broth, western blotting on the fibroblast cluster, or ECM secretion assay using immunohistochemistry.

Advantageous Effects of the Invention

According to embodiments regarding the fibroblast cluster or the method of preparing the same, a large amount of the 3D fibroblast cluster can be easily obtained in a culture container in a short time, and the 3D fibroblast cluster surrounded by extracellular matrix has an effect as a cell source to be utilized as an injection preparation for in vivo transplantation without damaging fiber cells.

According to embodiments regarding the in vitro 3D skin dermis model and the method of screening a drug by using the in vitro 3D skin dermis model, the in vitro 3D skin dermis model which is composes of 3D cell clusters can not only mimic the in vivo environments having structural and functional complexity of the skin, but also have an effect of screening a substance related to extracellular matrix including MMP or collagen at a high speed for high-throughput.

MODE OF THE INVENTION

Hereinafter, the present invention is described in detail with reference to Examples. However, Examples shown and described herein are illustrative examples of the present invention and are not intended to otherwise limit the scope of the inventive concept in any way.

Example 1: Formation of 3D Fibroblast Cluster and Analysis of Characteristics of the 3D Fibroblast Cluster In present Example, fibroblasts were cultured in a culture container including a surface coated with a fibroblast-binding protein, thereby forming a 3D fibroblast cluster.

Figure 1:
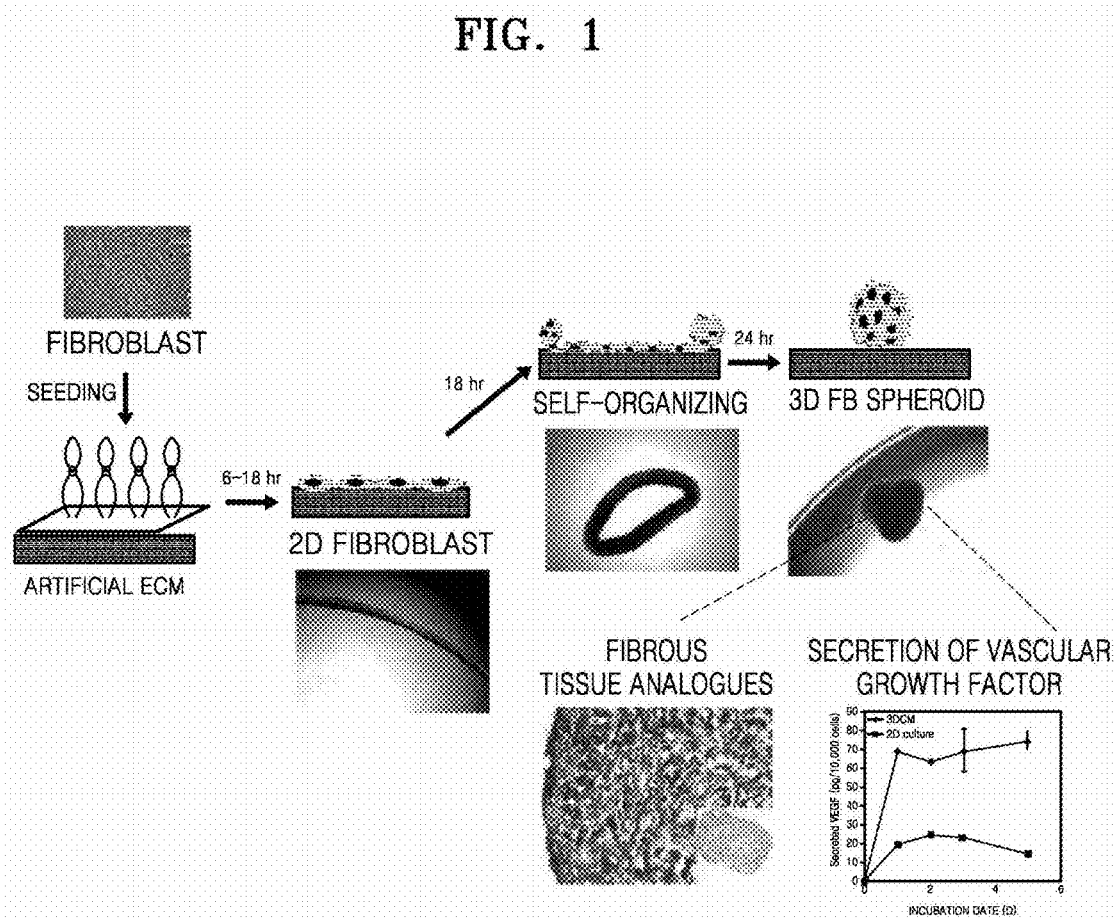
FIG. 1 is a schematic diagram showing a preparation process of a three-dimensional (3D) fibroblast cluster according to an embodiment.

FIG. 1 is a schematic diagram showing a preparation process of the 3D fibroblast cluster according to an embodiment.

Referring to FIG. 1, fibroblasts were seeded onto a culture container coated with MBP-FGF2. Then, the fibroblasts were cultured in a 2D manner on a surface of the culture container, and separated from the surface. Such separated or delocalized 2D fibroblast cluster was then continuously cultured while floating in the culture container, and after one day, a 3D fibroblast cluster was formed. The 3D fibroblast cluster formed according to an embodiment was confirmed to have capability of secreting an extracellular matrix and a vascular endothelial growth factor (VEGF). Hereinafter, the formation process of the 3D fibroblast cluster shown in FIG. 1, and methods and results of analyzing characteristics of the 3D fibroblast cluster will be described.

(1) Analysis of Cell Adhesion Characteristics of Fibroblasts and Morphological Changes of Fibroblasts after Adhesion To establish a culture method for inducing formation of a 3D fibroblast cluster, cell adhesion characteristics of fibroblasts, and cell adhesion signals and cell morphology upon adhesive features of fibroblasts were analyzed (1.1) Analysis of Cell Adhesion Characteristics of Fibroblasts A non-tissue culture treated 96-well plate (NTCP) (NTCP made of polystyrene and including a hydrophobic surface, Falcon Company) was coated with each of ECM fibronectin (20 µg/ml), MBP (10 µg/ml), MBP-VEGF (10 µg/ml), MBP-HBD (100 µg/ml), and MBP-FGF2 (10 µg/ml) for 4 hours, and then, washed three times with PBS. Afterwards, the NTCP was blocked with 100 µg/ml of BSA for 1 hour, and washed three times with PBS. $5 \times 10^4$ cells/cm$^2$ of fibroblasts per well were suspended in a serum-free DEME culture medium, and then, seeded onto the NTCP coated with each of the proteins above. The cells were subjected to lysis for 1 hour in an incubator at a temperature of 37° C., and the morphology of the cells was observed. The adhered cells were subjected to lysis by using a cell lysis buffer, and then, quantified by measuring each of the proteins according to bicinchoninic acid (BCA) assay.

Figure 2:
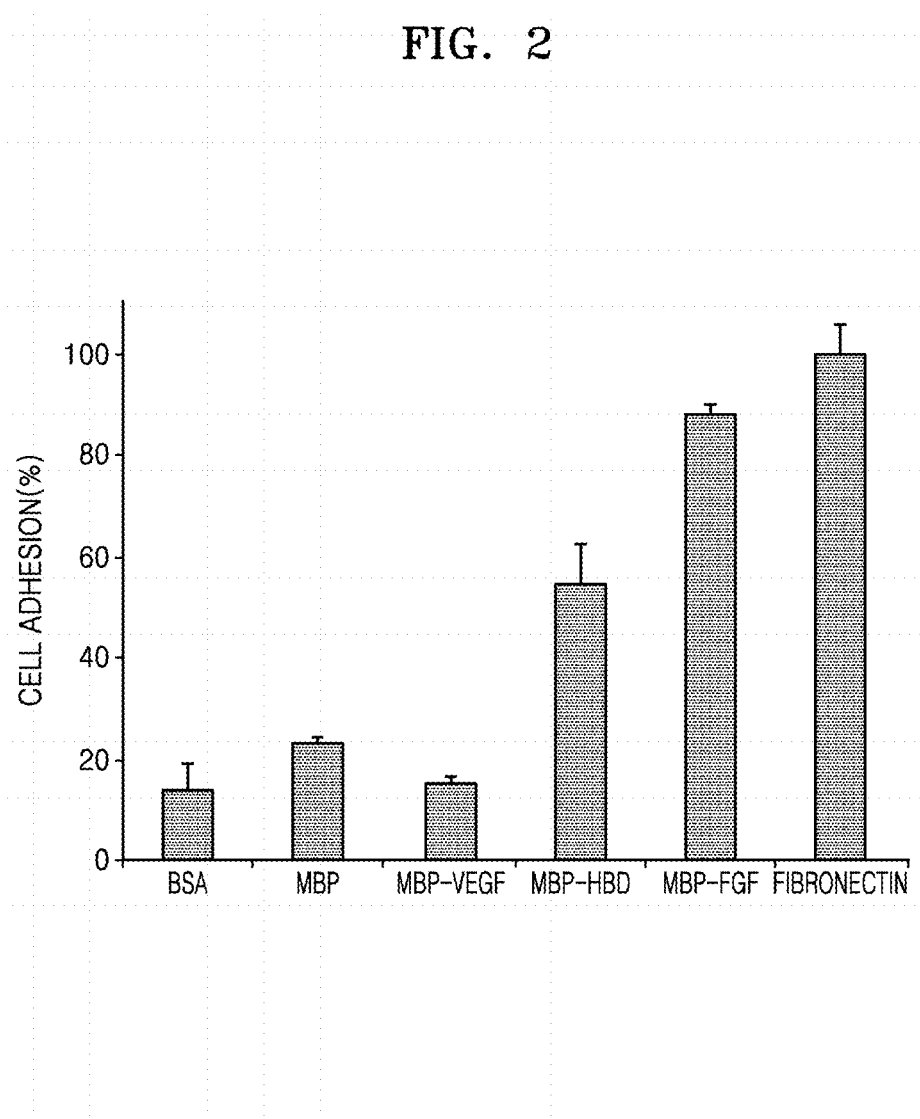
FIG. 2 is a graph showing cell adhesion levels of fibroblasts according to an embodiment, the levels being quantified according to contents of proteins.

FIG. 2 is a graph showing cell adhesion levels of the fibroblasts according to an embodiment, the levels being quantified according to contents of proteins.

As shown in FIG. 2, the NTCPs coated with BSA, MBP, and MBP-VEGF showed no cell adhesion. Meanwhile, 1 hour after the cell seeding, the NTCP coated with MBP-FGF2 showed a lower cell adhesion level than that of the NTCP coated with ECM-fibronectin, wherein ECM-fibronectin binds to integrins of a cell membrane.

(1.2) Analysis of Cell Morphology of Fibroblasts by Adhesiveness

To compare the cell morphology of the fibroblasts cultured in the NTCP according to Example 1(1.1) coated with each of fibronectin and MBP-FGF2, palloidin staining was performed on the fibroblasts that have been cultured for 30 minutes, 1 hour, and 4 hours after the adhesion.

Figure 3:
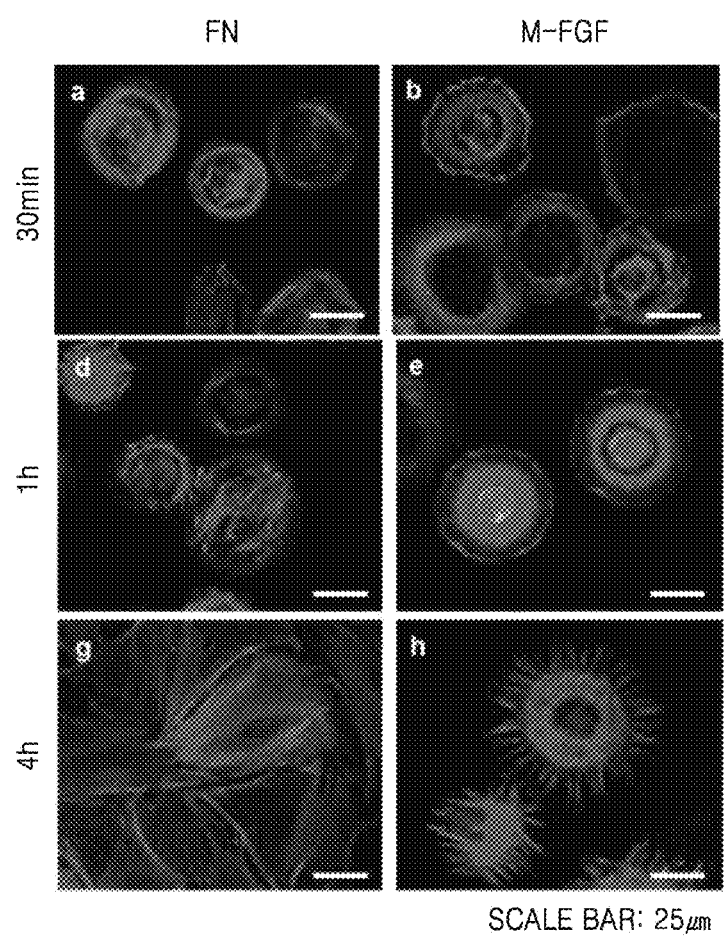
FIG. 3 shows fluorescence staining images of cell morphology of fibroblasts according to an embodiment.

FIG. 3 shows fluorescence staining images of the cell morphology of the fibroblasts according to an embodiment.

As shown in FIG. 3, it was confirmed that the fibroblasts adhered to MBP-FGF2 had a cytoskeleton that is not activated as much as that of the fibroblasts adhered to fibronectin. That is, as compared with the fibroblasts adhered to fibronectin, the fibroblasts adhered to MBP-FGF is meant to have limited activity in cell adhesion mediated by integrins, which are cell adhesion molecules present in a cell membrane.

(1.3) Analysis of Cell Adhesion Signals of Fibroblasts by Adhesiveness

To compare cell adhesion signals of the fibroblasts cultured in the NTCP according to Example 1(1.1) coated with each of fibronectin and MBP-FGF2, phosphorylation of focal adhesion kinase (FAK) in the fibroblasts was measured. To measure phosphorylation of FAK, the western blotting analysis using phospho-FAK antibody (Cell Signaling Company) was performed on the fibroblasts that have been cultured for 30 minutes, 1 hour, and 4 hours after the adhesion.

Figure 4:
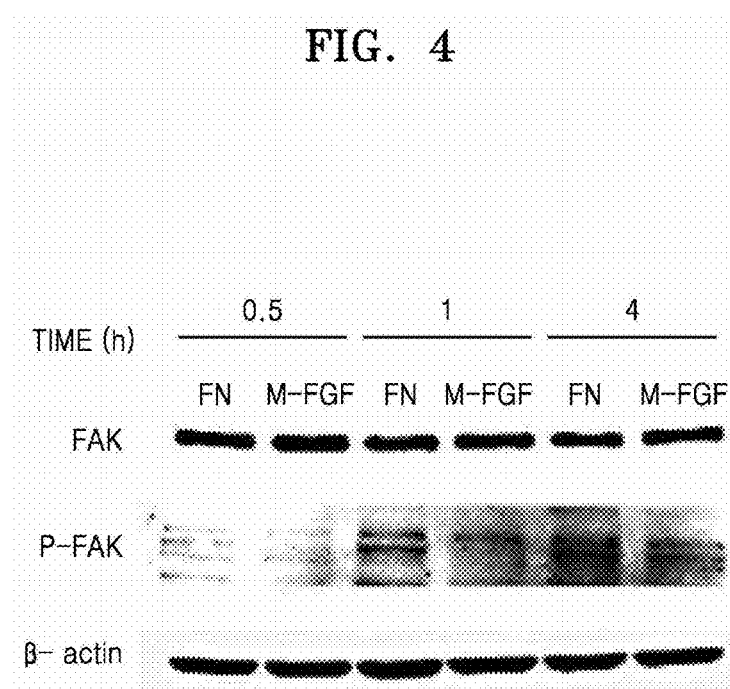
FIG. 4 shows results of phosphorylation activity of FAK in fibroblasts according to an embodiment.

FIG. 4 shows the phosphorylation activity of FAK in the fibroblasts according to an embodiment.

As shown in FIG. 4, it was confirmed that the fibroblasts adhered to MBP-FGF2 showed less phosphorylation of FAK than the fibroblasts adhered to fibronectin. That is, as compared with the fibroblasts adhered to fibronectin, the fibroblasts adhered to MBP-FGF is meant to have limited activity in cell adhesion mediated by integrins.

(2) Formation of 3D Fibroblast Cluster

Based on the results of Examples 1(1.3) to 1(1.3), a culture method for forming a 3D fibroblast cluster was established.

Fibroblasts were seeded onto each of 12, 24, 48, and 96-well NTCPs at a concentration of $0.5 \times 10^4$ cells/cm$^2$ to $1.5 \times 10^5$ cells/cm$^2$ per well, the NTCPs containing high-concentration glucose DMEM culture medium (FGM culture medium) and including a polystyrene surface coated with MBP-FGF2. The fibroblasts were then cultured in a stationary incubator at a temperature of 37° C. for 1, 2, and 3 days. The fibroblasts existing in the form of a sheet at the beginning of the culture were separated from the surface of the culture container over time, and accordingly the fibroblasts were present as a cell cluster from the first day of the culture and can be then easily collected by pipette without enzyme such as trypsin.

Figure 5:
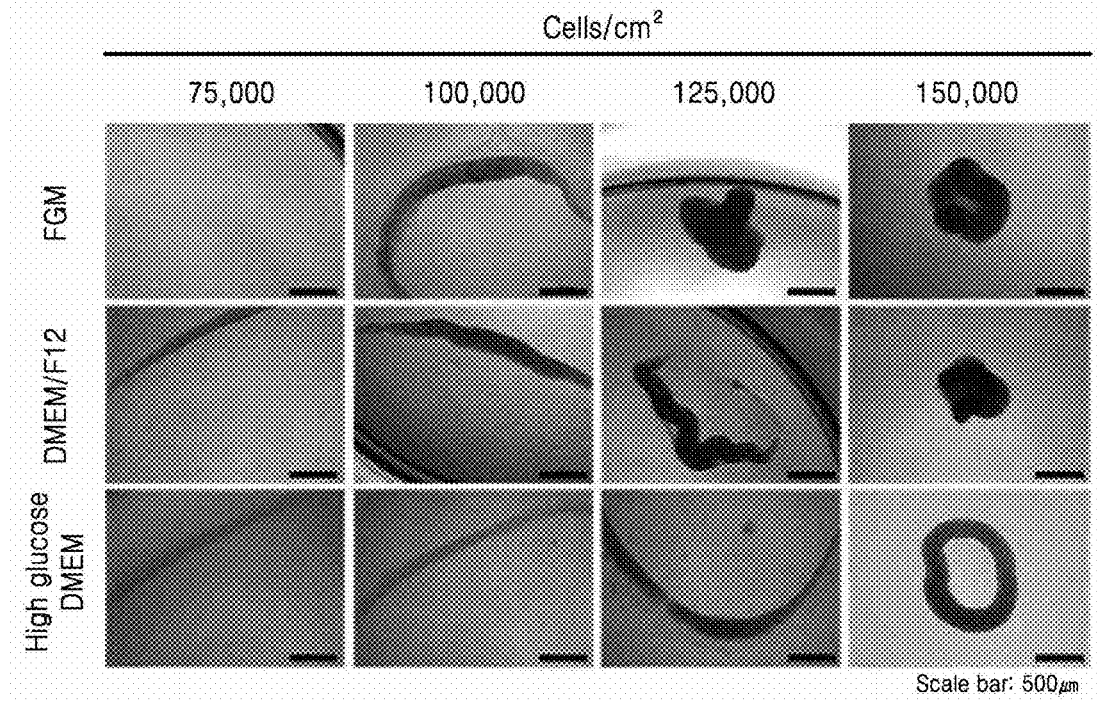
FIG. 5 is a diagram showing formation of a 3D fibroblast cluster according to an embodiment.

FIG. 5 is a diagram showing the formation of a 3D fibroblast cluster according to an embodiment.

As shown in FIG. 5, it was confirmed that, when cultured in the FGM culture medium, the formation of the 3D fibroblast cluster was effectively induced at a cell concentration of at least $1.25 \times 10^5$ cells/cm$^2$. When cultured under conditions of the culture at a lower cell concentration than the above, an intracellular distance required for the cell-cell interactions was not close enough so that a cell cluster may not be easily formed. A cell cluster may be also formed in a culture medium other than the FGM culture medium, but such a cell cluster formed therefrom may require a higher cell concentration than that of cells constituting the cell cluster formed in the FGM culture medium.

Figure 6:
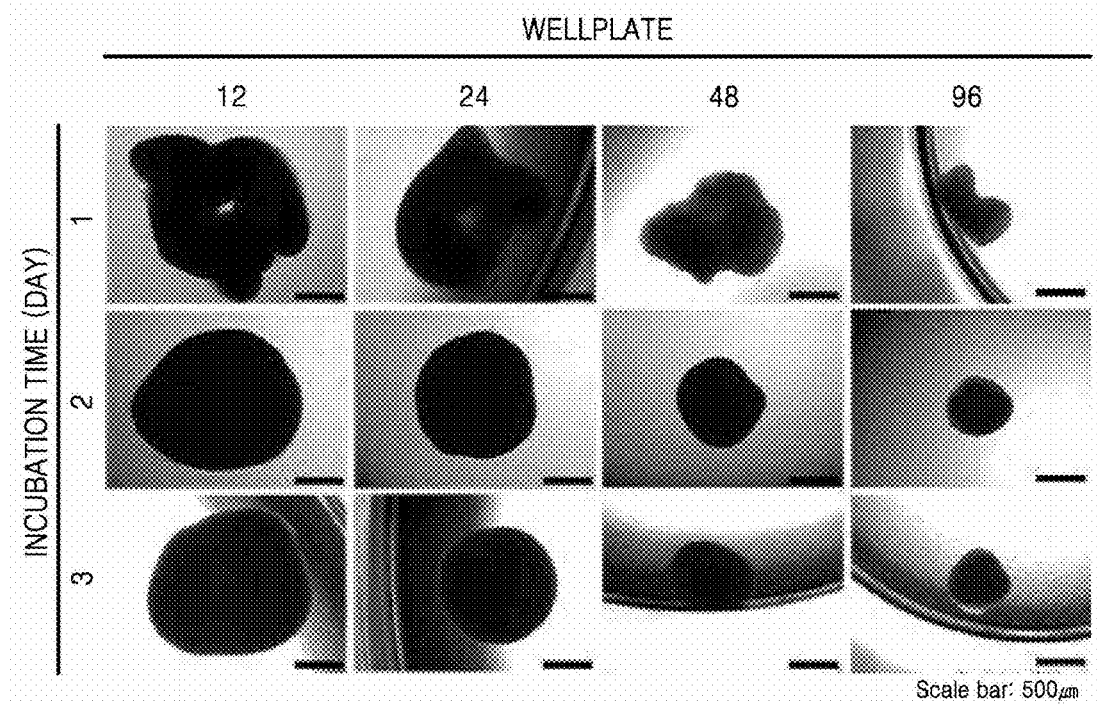
FIG. 6 is a diagram showing formation of a 3D fibroblast cluster according to an embodiment.

FIG. 6 is a diagram showing the formation of a 3D fibroblast cluster according to an embodiment.

As shown in FIG. 6, it was confirmed that, depending on a well size, a 3D spherical cell cluster having a size detectable with the naked eye on the surface coated with MBP-FGF2, for example, a size in a range of about 400 μm to about 1,000 μm, was formed.

(3) Analysis of Secretion Ability of 3D Fibroblast Cluster (3.1) Analysis of Ability of Extracellular Matrix (ECM) Secretion The 3D cell cluster formed by seeding cells at a concentration of $1.25 \times 10^5$ cells/cm$^2$ onto the NTCPs (12-well, 24-well, 48-well, and 96-well) of Examples 1(2) coated with various types of MBP-FGF2 was washed several times with PBS, and then, immobilized by treatment using 4% paraformaldehyde at room temperature for 30 minutes. Afterwards, the resulting 3D cell cluster was dehydrated with ethanol at various concentrations (50-100%), and then, embedded in paraffin. A paraffin block formed therefrom was cut to a thickness of 4 μm by using a microtome, fixed on a slide glass, and then, subjected to H&E staining and immunofluorescence staining with respect to fibronectin and collagen type I. The staining of collagen type I was carried out according to immunofluorescence staining. The prepared slide glass was first treated with BSA (4%) for 1 hour, and immersed in PBS containing primary antibodies overnight for a reaction. The slide glass was washed three times with PBS, and allowed again for a reaction with secondary antibodies for 1 hour in a dark room. Nuclear staining using DAPI was additional performed, and the results were analyzed by using a confocal microscope. Here, a control group was subjected to analysis performed under the same conditions, except that no primary antibody was used FIG. 7 shows the results of H&E staining on the 3D fibroblast cluster according to an embodiment.

Figure 7:
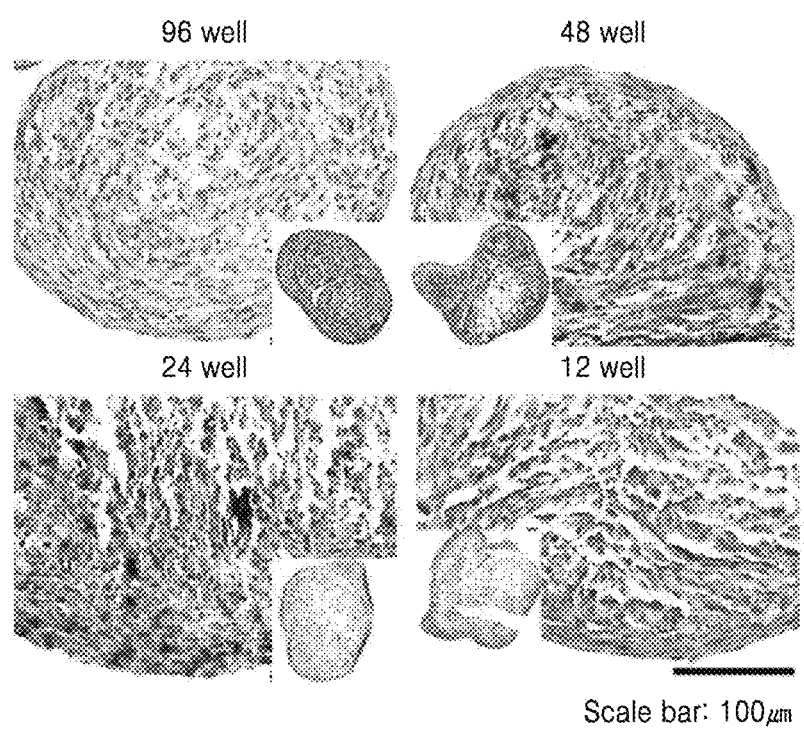
FIG. 7 shows results of Haematoxylin and Eosin (H&E) staining on a 3D fibroblast cluster according to an embodiment.

As shown in FIG. 7, it was confirmed that one day after the culture, fibroblasts treated at the same concentration in all wells formed a cell cluster.

Figure 8:
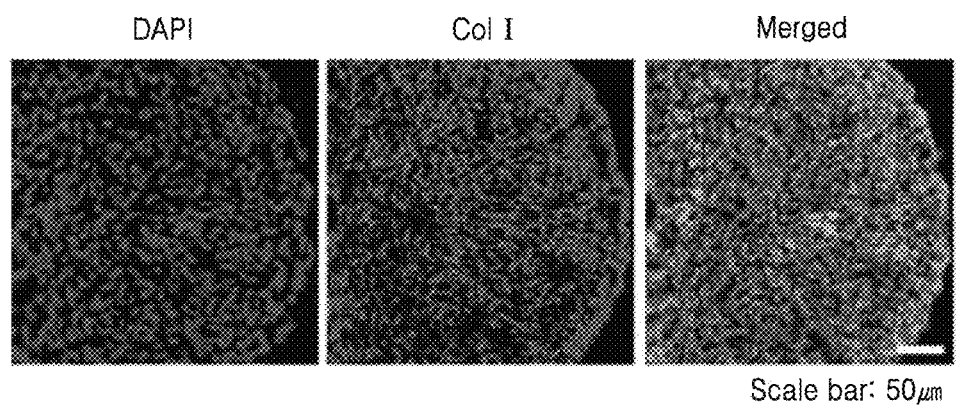
FIG. 8 shows results of immunofluorescence staining on collagen type I in a 3D fibroblast cluster according to an embodiment.

FIG. 8 shows the results of immunofluorescence staining on collagen type I in the 3D fibroblast cluster according to an embodiment.

As shown in FIG. 8, it was confirmed that collagen was stained throughout the 3D fibroblast cluster so that collagen was secreted during the formation of a cell cluster.

(3.2) Analysis of Levels of Vascular Endothelial Growth Factor (VEGF) Secretion

The 3D cell cluster formed by seeding cells at a concentration of $1.25 \times 10^5$ cells/cm$^2$ onto the of 96-well NTCP Example 1(2) coated with MBP-FGF2 were collected to measure levels of VEGF secretion.

Figure 9:
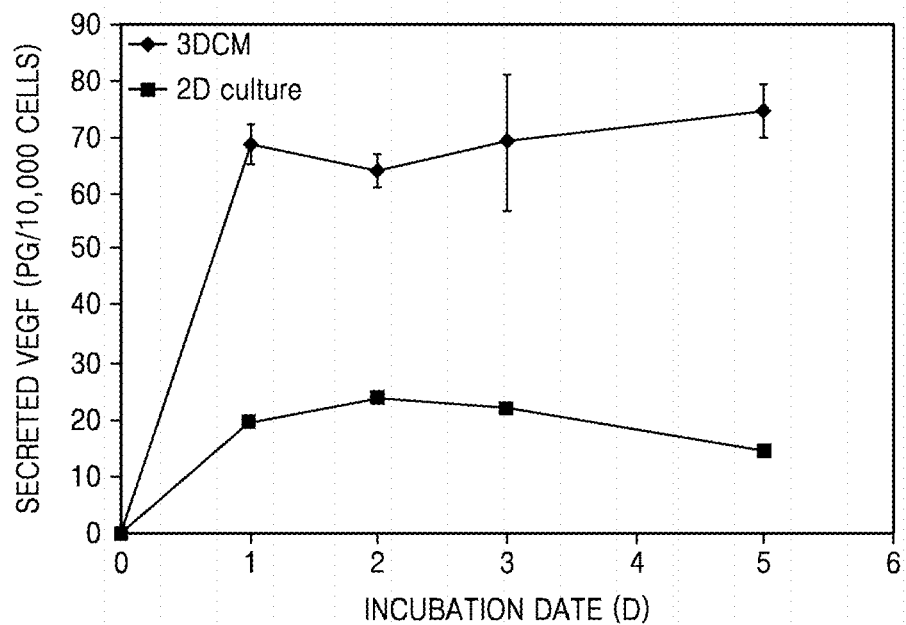
FIG. 9 is a diagram showing secretion levels of VEGF in a 3D fibroblast cluster according to an embodiment.

In detail, the formed 3D cell clusters were collected in tens, transferred to a 6-well NTCP, and then, washed once with PBS. Additionally, the cell clusters were washed once with FBS-free alpha MEM (Lonza Company), and alpha MEM (1.5 mL) was added thereto to be cultured in a stationary incubation for one day. Afterwards, a culture broth was obtained for each predetermined date, and an equivalent fresh culture broth was added. The VEFG present in the obtained culture broth was then quantified by using the ELISA kit (R&D Company). A method of using the kit was proceeded according to the supplier's protocol. FIG. 9 is a diagram showing the secretion levels of VEGF in the 3D fibroblast cluster according to an embodiment.

FIG. 9 is a diagram showing the secretion levels of VEGF in the 3D fibroblast cluster according to an embodiment.

As shown in FIG. 9, it was confirmed that the level of VEGF in the 3D fibroblast cluster increased more than twice as much as that of VEGF in the cells cultured in a 2D manner.

Example 2: Preparation of In Vitro 3D Artificial Dermis Model and Characterization of Dermis Model (1) Preparation of In Vitro 3D Artificial Dermis Model To prepare an in vitro 3D artificial dermis model, fibroblasts were first cultured. In detail, human dermal fibroblasts were cultured in high glucose Dulbecco's modified Eagle's medium (DMEM, Welgene, Daegu, South Korea) by using a tissue culture flask under conditions of 37° C., 5% $CO_2$, and 95% $O_2$ atmosphere. Human dermal fibroblasts of 5 passages were used for all experiments.

Next, a culture container for culturing fibroblasts in a 3D manner was prepared as follows. An NTCP (NTCP made of polystyrene and including a hydrophobic surface, Falcon Company) was coated with maltose binding protein (MBP)-fibroblast growth factor (FGF) (20 μg/ml) at room temperature for 4 hours. The NTCP was washed three times with PBS, and then, unbound MBP-FGF was removed therefrom. A detailed manufacturing method for the culture container is disclosed in KR 10-2010-0122778, which is incorporated herein by reference in its entirety.

Figure 10:
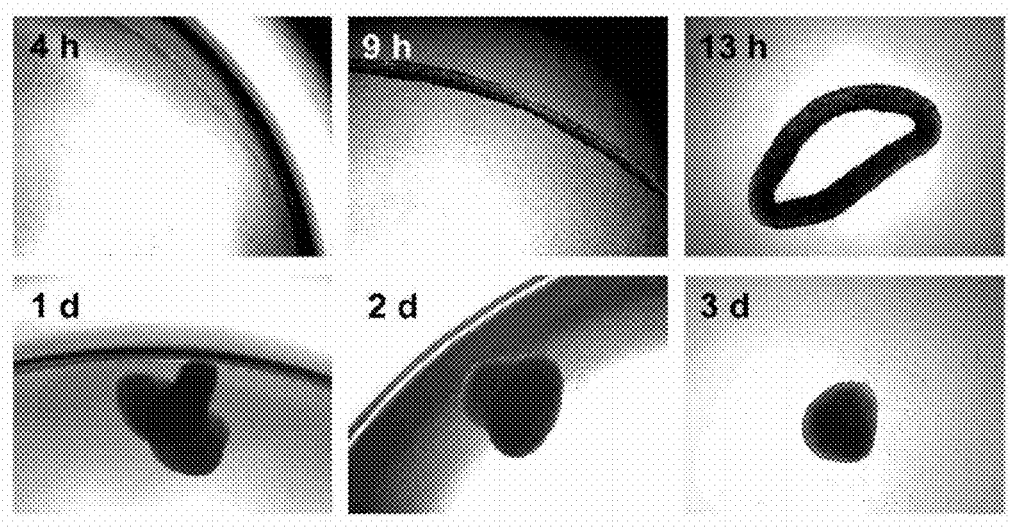
FIG. 10 is a diagram showing microscopic observation of a formation process of a 3D fibroblast cluster according to an embodiment.

The fibroblasts were seeded onto the culture container, thereby preparing a 3D fibroblast cluster. In detail, fibroblasts were seeded onto the 96-well NTCP containing fibroblast growth medium (FGM, Lonza) at a concentration of $1.25 \times 10^5$ cells/cm$^2$ per well, and cultured at a temperature of 37° C. The fibroblasts were cultured in a 2D manner on a surface of the culture container, and separated from the surface. Such separated or delocalized 2D fibroblast cluster was then continuously cultured while floating in the culture container, and within 24 hours, a 3D fibroblast cluster was formed spontaneously. The formed 3D fibroblast cluster was collected on the 1$^{st}$ day (Day 1), 3$^{rd}$ day (Day 3), and 5$^{th}$ day (Day 5) of the culture. The formation of the 3D fibroblast cluster consisting of adhesive fibroblasts was observed with a phase contrast microscope (Carl Zeiss, Germany), and the results are shown in FIG. 10. Hereinafter, the 3D fibroblast cluster was represented by '3DCM'.

In addition, as a comparative example, the fibroblasts were cultured in a 2D manner. In detail, $1.25 \times 10^5$ cells/cm$^2$ of adipose stem cells were inoculated into each well of a 96-well tissue culture plate (TCP), and cultured in a fibroblast growth medium (FGM, Lonza Company). In the same manner as in the 3D cell cluster, cells were collected on the 1$^{st}$ day (Day 1), 3$^{rd}$ day (Day 3), and 5$^{th}$ day (Day 5) of the culture for analysis of characteristics of an artificial dermis model. Hereinafter, the cells cultured in a 2D manner are represented by '2D cells'.

FIG. 10 is a diagram showing the microscopic observation of the formation process of a 3D fibroblast cluster according to an embodiment.

As shown in FIG. 10, it was confirmed that a 3D spherical cell cluster having a size detectable with the naked eye, for example, a size in a range of about 400 μm to about 1,000 μm, was formed.

(2) Analysis of Characteristics of In Vitro 3D Artificial Dermis Model

The following experiment was carried out to analyze the characteristics of the 3D fibroblast cluster prepared above.

(2.1) Analysis of Expression of Extracellular Matrix (ECM) Gene in 3D Fibroblast Cluster To analyze expression amounts of ECM-related genes, such as genes of collagen, fibronectin, and elastin, qantitative real-time polymerase chain reaction (qRT-PCR) was used.

In detail, total RNAs were extracted from the 3D cell cluster and the 2D cells at different times (on the $1^{st}$, $3^{rd}$, and $5^{th}$ day of the culture) according to the manufacturer's instructions using a Qiagen miniprep kit (Qiagen Inc., USA). The extracted RNAs were dissolved in nuclease-free water, and then, the concentration of the resulting RNAs was quantified using a NanoDrop ND1000 spectrophotometer (Thermo Fisher Scientific). Here, synthesis of complementary DNA was performed by using Maxime RT PreMix (iNtRon, South Korea) according to the manufacturer's instructions. All target primers were purchased from Bioneer (South Korea). All polymerase chain reactions were performed using ABI Prism 7500 (Applied Biosystems), and gene expression levels were quantified using SYBR Premix Ex Taq (TaKaRa, Japan). Relative gene expression levels were calculated using the comparative (Ct) method, and the results are shown in FIG. 11.

Figure 11:
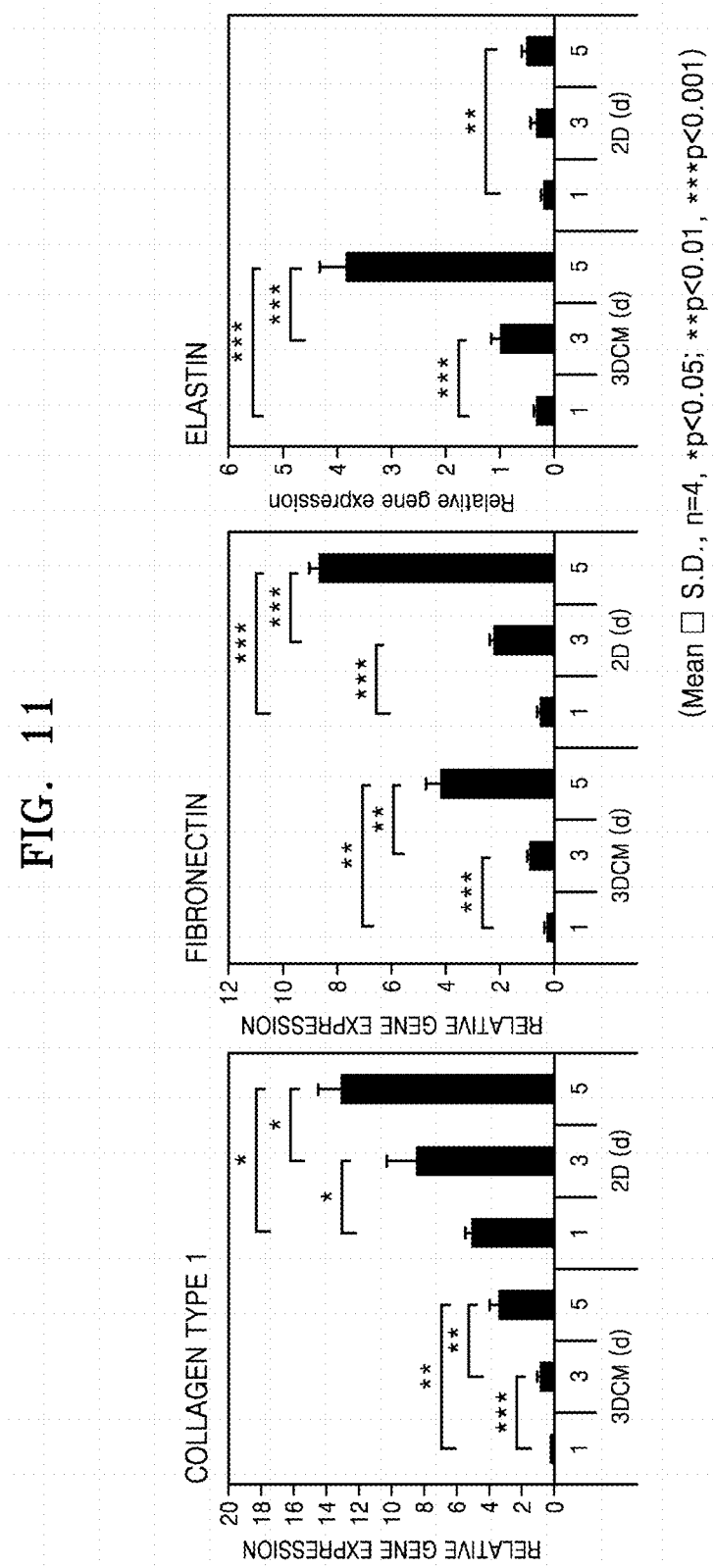
FIG. 11 is a graph showing relative expression levels of extracellular matrix-related genes in a 3D fibroblast cluster according to an embodiment.

FIG. 11 is a graph showing relative expression levels of ECM-related genes in a 3D fibroblast cluster according to an embodiment.

As shown in FIG. 11, it was confirmed that expression levels of genes of collagen type I and fibronectin were almost three times lower in the 3D cell clusters than those of genes of collagen type I and fibronectin in the 2Dcells, and that expression levels of genes of elastin increased in the 3D cell cluster as compared with those of genes of elastin in the 3D cell cluster. In particular, in the case of elastin, the expression levels of genes thereof were similar in the 2D cells and the 3D cell cluster on the first day of the culture. However, from the third day of the culture, the expression levels of genes of elastin significantly increased in the 3D cell cluster. Consequently, it was confirmed that, in the 3D fibroblast cluster according to an embodiment, the expression of collagen and fibronectin decreased, whereas the expression of elastin increased. Thus, the 3D fibroblast cluster was able to mimic the environment of skin dermis, and accordingly, was able to be utilized for the development of materials targeting the 3D fibroblast cluster.

(2.2) Analysis of Collagen Expression by 3D Fibroblast Cluster

To analyze collagen in the 3D fibroblast cluster, hydroxyproline assay, immunostaining, and western blotting were performed on the 3D fibroblast cluster.

In detail, for the hydroxyproline assay, RIPA buffer (Sigma-Aldrich) was used to collect 2D cells and 3D cell clusters (including $3 \times 10^6$ cells) at different times (on the $1^{st}$, $3^{rd}$, and $5^{th}$ day of the culture), and the collected cells 2D cells and 3D cell clusters were hydrolyzed in a 12 N HCl solution at a temperature of 120° C. for 3 hours. The assay was performed according to the manufacturer's instructions using a hydroxyproline kit (Sigma-Aldrich). Here, the absorbance was measured using a Multisakn meter (Thermo) at 560 nm, and the results are shown in FIG. 12.

For the immunostaining, the 3D cell clusters and 2D cells collected at different times were washed three times with PBS, and immobilized with 4% PFA for 30 minutes. Then, the resulting product was embedded in an optimal cutting temperature (OCT) compound (TISSUE-TEK° 4583; Sakura Finetek USA, Inc.), frozen at a temperature of −28° C., and cut to a thickness of 6 μm. To avoid nonspecific binding thereto, a section was incubated in BSA (4%) at room temperature for 1 hour. Afterwards, the section was incubated overnight at a temperature of 4° C. with primary antibodies (Rabit, Abicam) that were specific to collagen type I. Then, a sample on the section was washed with PBS, and incubated for 1 hour with corresponding fluorescent conjugated secondary antibodies (Donkey anti-rabbit)(Life Technologies) in 1% BSA. In addition, 4,5-diamino-2-phenylindole (DAPI) (Vector Laboratories) was used for nuclear staining. Here, a control group was subjected to experiments performed under the same conditions, except that no primary antibody was used, and was observed with a confocal microscope (Carl Zeiss). The results are shown in FIG. 13.

For the western blotting, the same cultured cells as the above were soluble in RIPA buffer (Sigma-Aldrich) together with a protease inhibitor cocktail. Afterwards, the lysate was centrifuged at a speed of 15,000 g at a temperature of 4° C. for 30 minutes, diluted with a Laemmli sample containing 2% SDS and 5% (v/v) 2-mercaptoethanol, and then, heated at a temperature of 90° C. for 5 minutes. The proteins were separated by SCD-polyacrylamide gel electrophoresis (SDS-PAGE) with use of 10% resolving gel, and transferred to a nitrocellulose membrane (Bio-Rad, USA). The membrane was then incubated overnight at a temperature of 4° C. with primary antibodies that are specific to collagen type I (Colla1, Boster Bio CO. Ltd) and β-actin (Santan Cruz Biotechnology). For detection, the membrane was incubated with peroxidase-conjugate antibodies (Santa Cruz Biotechnology) at room temperature for 1 hour. Scanning was then performed thereon by using an imaging analyzer (LSA3000, Fujifilm) to form a chemiluminescence image, and the results are shown in FIG. 14.

Figure 12:
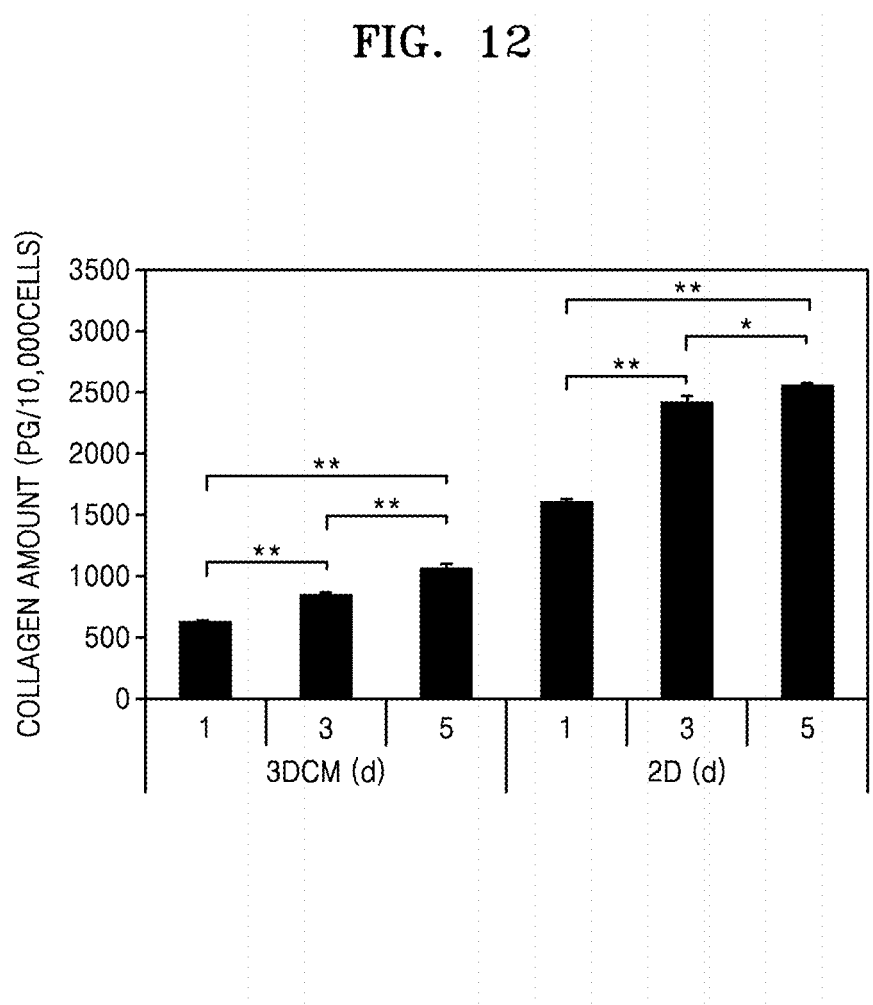
FIG. 12 is a graph showing hydroxyproline assay results of measuring a collagen amount in a 3D fibroblast cluster according to an embodiment.

FIG. 12 is a graph showing the hydroxyproline assay results measuring a collagen amount in a 3D fibroblast cluster according to an embodiment.

Figure 13:
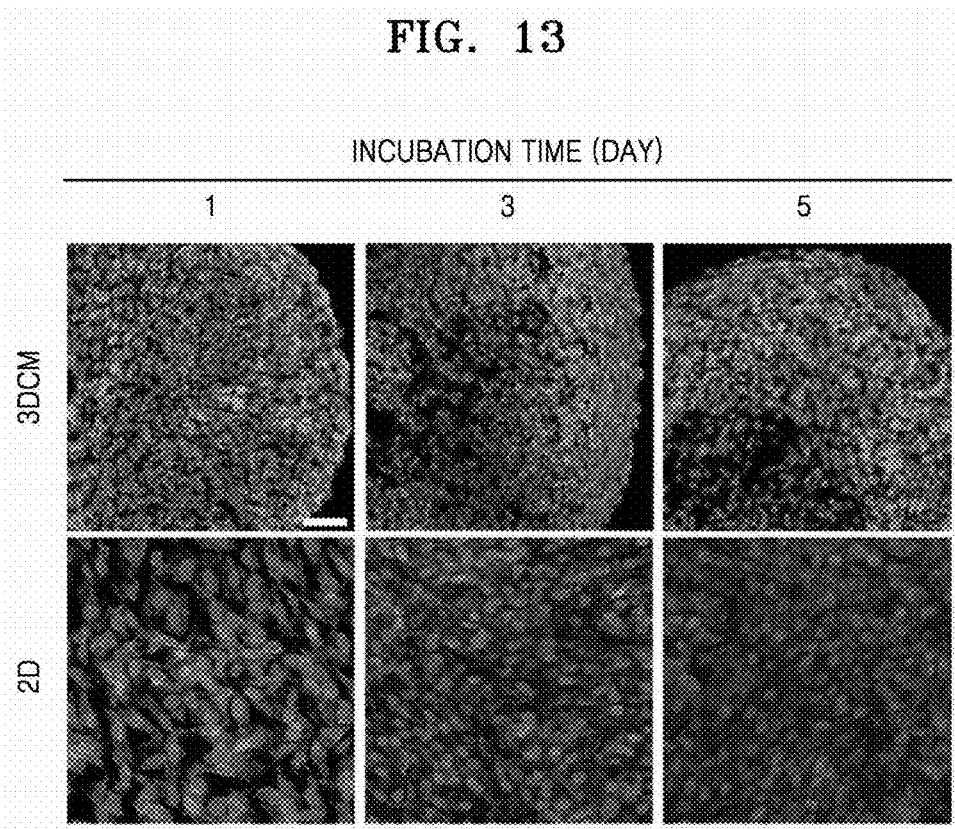
FIG. 13 is a graph showing immunostaining results of measuring an expression level of collagen type I in a 3D fibroblast cluster according to an embodiment.

FIG. 13 is a graph showing the immunostaining results of measuring an expression level of collagen type I in a 3D fibroblast cluster according to an embodiment.

Figure 14:
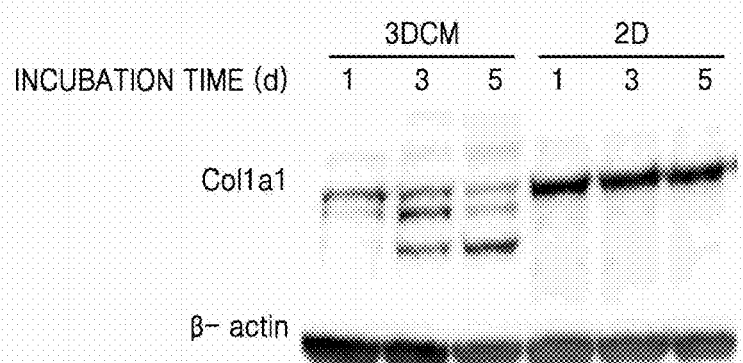
FIG. 14 is a diagram showing western blotting results of measuring an expression level of collagen type I in a 3D fibroblast cluster according to an embodiment.

FIG. 14 is a diagram showing the western blotting results of measuring an expression level of collagen type I in a 3D fibroblast cluster according to an embodiment.

As shown in FIG. 12, it was confirmed that the total amount of collagen secreted in the 3D cell cluster increased with increasing incubation time, but were reduced as compared with that of collagen secreted in the 2D cells. The results are consistent with the results of Example 2(2.1).

In addition, as shown in FIG. 13, the staining of collagen type I decreased during the culture of the 3D cell cluster, whereas the staining did not decrease in the 2D cells. The results refer that collagen type I had been degraded during the culture in a 3D culture system.

In addition, as shown in FIG. 14 and in the same manner as in the results shown in FIG. 12, collagen type I was fragmented during the culture of 3D cell cluster, whereas such fragmentation did not occur in the 2D cells.

Based on the results above, it was confirmed that the expression of collagen was decreased in the 3D fibroblast cluster according to an embodiment so that the 3D fibroblast cluster can be utilized for screening a candidate material for increasing the collagen amount.

(2.3) Analysis of MMP Expression by 3D Fibroblast Cluster

To analyze expression of MMP by the 3D fibroblast cluster, RT-PCR 音 was performed in the same manner as in Example 2(2.1), and the results are shown in FIG. 15A.

In addition, to analyze total secretion amounts of MMP-1, ELISA was performed. In detail, a culture medium was prepared with normal 2D cells and 3D cell cluster (3DCM) at different times ($1^{st}$ day, $3^{rd}$ day, and $5^{th}$ day). The assay was performed thereon by using the Quantikine ELISA kit for human total MMP 1 (R&D System) according to the manufacturer's instructions. Here, the absorbance was measured by using a Multisakn (Thermo) at 560 nm, and the results are shown in FIG. 15B.

Figure 15:
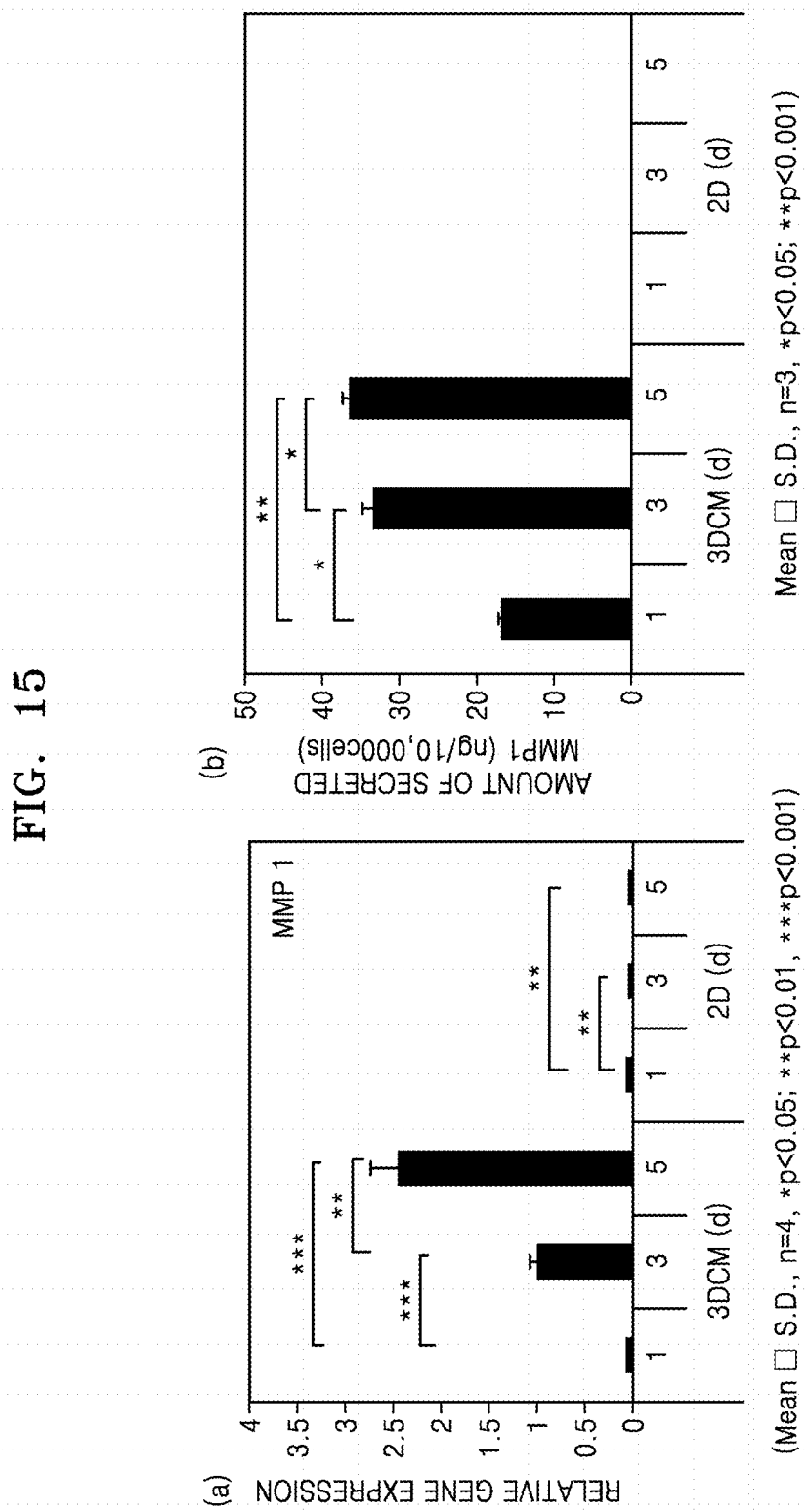
FIG. 15 is a graph showing expression levels and secretion levels of MMP 1 by a 3D fibroblast cluster according to an embodiment.

FIG. 15 is a graph showing expression levels and secretion levels of MMP1 by the 3D fibroblast cluster according to an embodiment.

As shown in FIG. 15, the expression level of MMP 1 gene was significantly increased in the 3D cell cluster, as compared with that in the 2D cells. In addition, as shown in the ELISA assay the secretion level of MMP 1 was significantly increased in the 3D cell cluster, as compared with that in 2D cells. Consequently, it was confirmed that the fibroblast cluster according to an embodiment showing significantly increased expression of MMP can be effectively utilized for the development of a substance targeting the MMP.

(3) Evaluation of Inhibitory Effect of MMP Inhibitor by Using 3D Fibroblast Cluster To additionally determine whether the 3D fibroblast cluster according to an embodiment was usable for screening an MMP inhibitor, the 3D fibroblast cluster was treated with the existing MMP inhibitors already known in the art, and then, the secretion of MMP was confirmed.

In detail, the 3D fibroblast cluster of the culture at Day 1 prepared according to Example 2(1) was inoculated with retinoic acid (10 mM), abietic acid (100 mM), transforming growth factor-b1 (TGF-b1) (5 ng/ml) that were diluted in a fibroblast growth factor (FGM, Lonza Company). The inoculated 3D fibroblast cluster was then cultured in a stationary incubator at a temperature of 37° C. for 2 and 4 days, separately. The culture broth was recovered therefrom, and was subjected to measurement of secretion of MMP1. Through the measurement, the culture broth was quantified by using the ELISA kit (R&D Company), wherein a method of using the kit was proceeded according to the supplier's protocol. The results thus obtained are shown in FIG. 16.

As a control group for the 3D fibroblast cluster and for the comparison of the inhibitory effect of MMP inhibitors using the two-dimensionally cultured fibroblasts, fibroblasts irradiated with ultraviolet B (UVB) were used. In detail, fibroblasts that were suspended in high-concentration glucose DMEM were seeded onto each well of a tissue culture treated 6-well plate at a concentration of $2.5 \times 10^5$ cells/cm$^2$, and then, cultured in a stationary incubator at a temperature of 37° C. for 1 day. Next, a washing process was performed thereon three times by using PBS, a serum-free MEM medium was added thereto, and the fibroblasts were cultured in a stationary incubator at a temperature of 37° C. for 1 hour. After a washing process was performed thereon three times by using PBS, to induce overexpression of MMP1, UVB (20 mJ/cm$^2$) was irradiated thereto. Following UV irradiation, the resulting fibroblasts were inoculated with various concentrations of retinoic acid (2, 10, 40 mM), abietic acid (20, 100, 400 mM), and TGF-b1 (1, 5, 20, ng/ml) that were diluted in a fibroblast growth medium (FGM, Lonza Company). The inoculated fibroblasts were then additionally cultured in a stationary incubator at a temperature of 37° C. for 2 days. The culture broth was recovered therefrom, and was subjected to measurement of secretion of MMP1. Through the measurement, the culture broth was quantified by using the ELISA kit (R&D Company), wherein a method of using the kit was proceeded according to the supplier's protocol. The results thus obtained are shown in FIG. 17.

Figure 16:
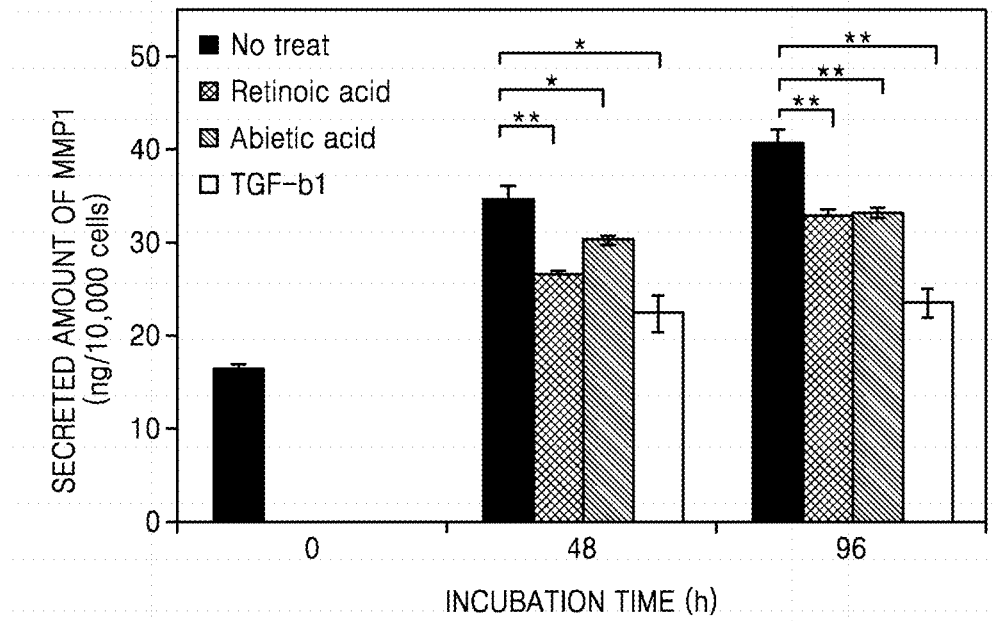
FIG. 16 is a graph showing secretion levels of MMP1 in cells after the cells are treated with an MMP1 inhibitor in a 3D fibroblast cluster according to an embodiment.

FIG. 16 is a graph showing secretion levels of MMP1 in cells after the cells were treated with an MMP1 inhibitor in a 3D fibroblast cluster according to an embodiment.

Figure 17:
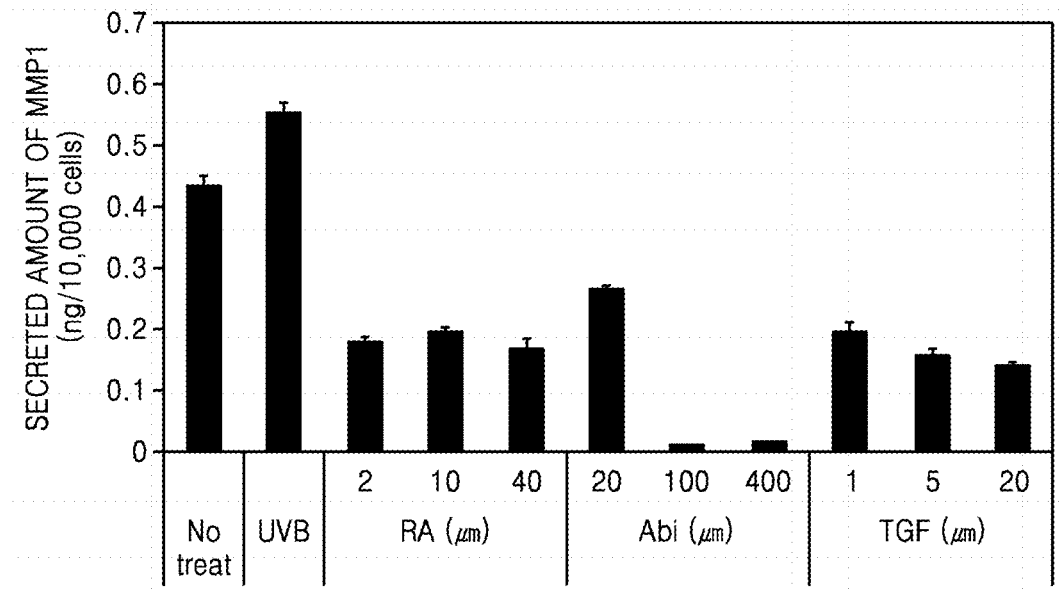
FIG. 17 is a graph showing secretion levels of MMP1 in cells, after fibroblasts that are cultured two-dimensionally and irradiated with ultraviolet rays to induce overexpression of MMP1 was treated with an MMP1 inhibitor.

FIG. 17 is a graph showing secretion levels of MMP1 in cells, after fibroblasts that are cultured two-dimensionally and irradiated with ultraviolet rays to induce overexpression of MMP1 was treated with an MMP1 inhibitor.

As shown in FIG. 16, after an incubation period of 2 days and 4 days, the secretion levels of MMP1 in the fibroblast cluster that was not treated with the MMP1 inhibitor was increased to about 2.1 times and about 2.4 times, respectively. However, the secretion levels of MMP1 in the fibroblast cluster treated with retinoic acid and abietic acid were each about 80% and 81% of those of MMP1 in the control group. The secreted amount of MMP1 in the fibroblasts treated with TGF-b1 was about 60% of that of MMP1 in the control group.

As shown in FIG. 17, the secreted amount of MMP1 in the fibroblasts that were cultured two-dimensionally and irradiated with UVB was increased to about 1.3 times the fibroblasts that were not irradiated with UV rays. However, the secreted amount of MMP1 in the fibroblasts that were treated with retinoic acid was reduced to about 30% of that of MMP1 in the control group. In comparison with the fibroblasts treated with TGF-b1, depending on the amount of the TGF-b1 used for the treatment, the secreted amount of MMP1 therein was reduced to about 25-35% of that of MMP1 in the control group. In particular, when the fibroblasts were treated with abietic acid, for example, treated at a concentration of 20 mM of abietic acid, the secreted amount of MMP1 was approximately reduced to half of that of MMP1 in the control group, However, when the fibroblasts were treated with abietic acid at a concentration of at least 100 mM, the secreted amount of MMP1 was about 2% of the that of MMP1 in the control group. In comparison with the results obtained by using the 3D cell cluster, the tendency of reduced secretion amount upon the treatment of the inhibitor is the same. However, in comparison with the 3D cell cluster, the decrease of the MMP inhibitor in the 2D cells was higher about 2.7 times (retinoic acid-treated fibroblasts), about 1.7 to 2.4 times (TGF-b1-treated fibroblasts), and about 1.7 to about 40 times (abietic acid-treated fibroblasts) the control group.

Consequently, it was confirmed that, the 2D cells were not suitable for drug screening due to significantly high drug sensitivity, and that the 3D cell cluster was effectively usable for screening a drug including the MMP inhibitor.

Figure 18:
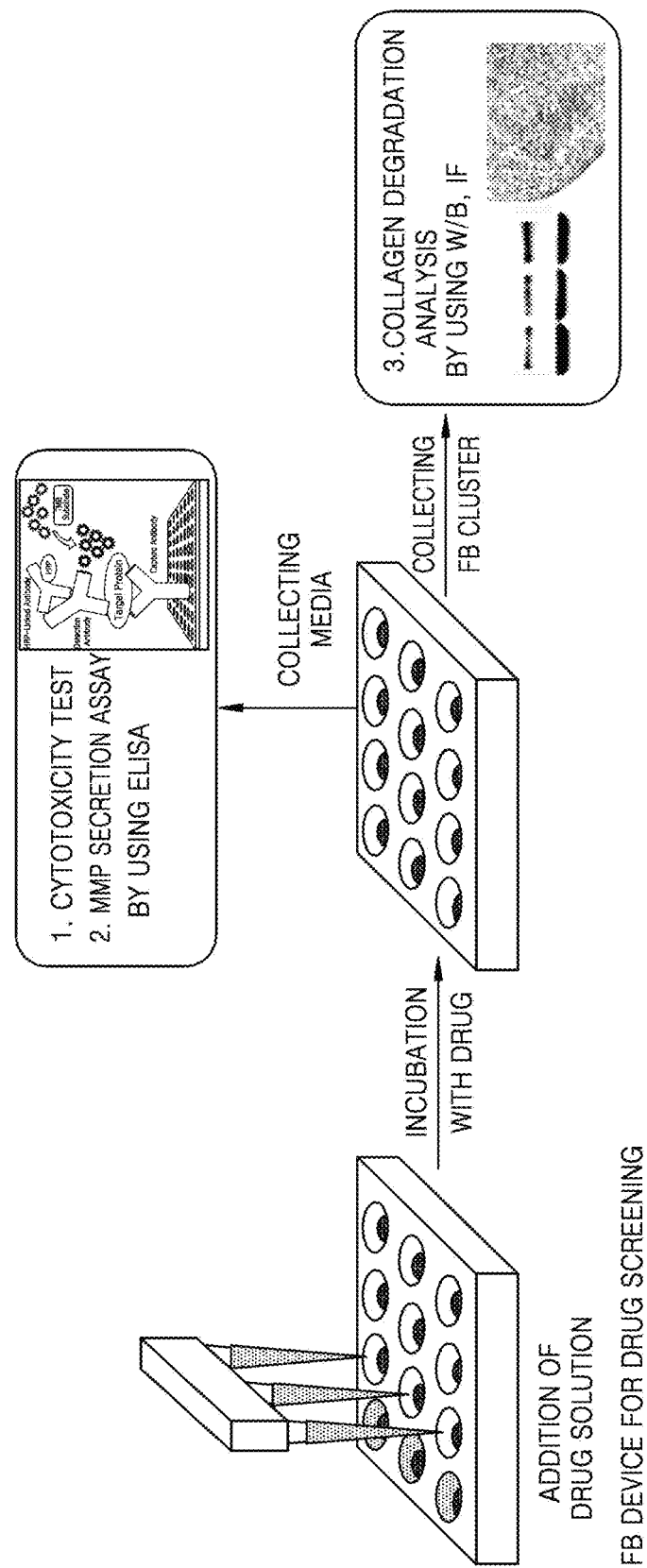
FIG. 18 is a schematic diagram showing a drug-screening device including a 3D fibroblast cluster according to an embodiment, and a method of screening a drug by using the drug-screening device.

FIG. 18 is a schematic diagram showing a drug-screening device including a 3D fibroblast cluster according to an embodiment, and a method of screening a drug by using the drug-screening device. Referring to FIG. 18, there is provided the drug-screening device including a well plate having at least one well, wherein one or more 3D fibroblast clusters according to an embodiment are seeded per well. The 3D fibroblast cluster may include $3.0 \times 10^5$ cells to about $1.0 \times 10^6$ cells. In addition, the 3D fibroblast cluster may have a diameter in a range of about 300 μm to about 2,000 μm, and may be formed into spheres (including spheroids) or sheets. The drug, i.e., the candidate substance, is the same as described above. The present inventive concept also provides a method of screening a drug, the method including: injecting a solution containing a candidate substance per well of a cell plate included in the drug-screening device; culturing the well plate to which the candidate substance is injected; collecting a fibroblast cluster from the well plate or recovering a culture broth from the well plate; and performing assay on the collected fibroblast cluster or on the culture broth. Here, the candidate substance may be identical to or different from the candidate substance described above. Regarding the culturing of the well plate, culture time and temperature may be arbitrarily determined by one of ordinary skill in the art. The assay performed herein may be, for example, MMP secretion assay using ELISA on the culture broth, western blotting on the fibroblast cluster, or ECM secretion assay using immunohistochemistry.

The invention claimed is:

1. A method of producing a fibroblast cluster, the method comprising:
   culturing fibroblasts in a culture broth in a culture container having a surface coated with a protein having fibroblast-binding activity;
   obtaining a culture including a fibroblast cluster that is formed by detaching the cultured fibroblasts from the surface; and
   separating the fibroblast cluster from the culture,
   wherein binding between the protein having fibroblast-binding activity and fibroblasts is weaker than binding between fibroblasts.

2. The method of claim 1, wherein, in the culturing of fibroblast, the fibroblast is initially adhered to the surface of the culture container for proliferation, but as growing, the fibroblast is detached from the surface of the culture container.

3. The method of claim 1, wherein the protein having fibroblast-binding activity weakly binds to the fibroblast as compared with binding between fibroblast and a fibronectin in the culture broth.

4. The method of claim 1, wherein the protein having fibroblast-binding activity does not bind to integrin present in a cell membrane of the fibroblast.

5. The method of claim 1, wherein the protein having fibroblast-binding activity binds to heparan sulfate proteoglycan present in a cell membrane of the fibroblast.

6. The method of claim 1, wherein the protein having fibroblast-binding activity is a fibroblast growth factor (FGF).

7. The method of claim 1, wherein the protein is immobilized on the surface of the culture container by connecting the protein to one of the group consisting of a maltose-binding protein (MBP), hydrophobin, and a hydrophobic cell penetrating peptide (CPP), or a combination thereof.

8. The method of claim 1, wherein the surface of the culture container is a hydrophobic surface selected from the group consisting of a silanized surface, a hydrocarbon coated surface, a polymer surface, and a metallic surface.

9. The method of claim 1, wherein the culturing of the fibroblast is performed for 1 day to 1 week.

10. The method of claim 1, wherein the separating of the formed fibroblast cluster from the culture is carried out without treatment of enzyme.

11. A method of preparing an in vitro three-dimensional (3D) artificial skin model, the method comprising:
    culturing fibroblasts in a culture broth container having a surface coated with a protein having fibroblast-binding activity to thereby obtain a culture including a fibroblast cluster that is formed by detaching the cultured fibroblasts from the surface, wherein binding between the protein having fibroblast-binding activity and fibroblasts is weaker than binding between fibroblasts; and
    further culturing the fibroblast cluster from the obtained culture for at least 12 hours.

12. The method of claim 11, wherein the protein having fibroblast-binding activity does not bind to integrin present in a cell membrane of the fibroblasts.

13. The method of claim 11, wherein the fibroblast cluster that is further cultured for at least 12 hours decreases expression or activity of collagen, or increases activity or expression of matrix metalloproteinase (MMP).

14. The method of claim 11, the fibroblast cluster additionally decreases expression or activity of fibronectin, or increases expression or activity of elastin.

* * * * *